United States Patent
Paffel et al.

(10) Patent No.: US 10,147,502 B2
(45) Date of Patent: Dec. 4, 2018

(54) DATA DRIVEN SCHEMA FOR PATIENT DATA EXCHANGE SYSTEM

(71) Applicant: Medtronic, Inc., Minneapolis, MN (US)

(72) Inventors: Timothy D. Paffel, Shafer, MN (US); William C. Harding, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 311 days.

(21) Appl. No.: 15/289,655

(22) Filed: Oct. 10, 2016

(65) Prior Publication Data

US 2017/0098041 A1    Apr. 6, 2017

Related U.S. Application Data

(63) Continuation of application No. 14/464,357, filed on Aug. 20, 2014, now Pat. No. 9,467,450.

(Continued)

(51) Int. Cl.
*G16H 10/60* (2018.01)
*G06F 19/00* (2018.01)
*H04L 29/06* (2006.01)

(52) U.S. Cl.
CPC ............. *G16H 10/60* (2018.01); *G06F 19/00* (2013.01); *H04L 63/0428* (2013.01); *H04L 63/10* (2013.01); *H04L 63/20* (2013.01)

(58) Field of Classification Search
CPC ..... G16H 10/60; G06F 19/00; H04L 63/0428; H04L 63/20; H04L 63/10
See application file for complete search history.

(56) References Cited

U.S. PATENT DOCUMENTS 7,155,290 B2    12/2006    Von Arx
7,685,511 B2     3/2010    Mysore
(Continued)

FOREIGN PATENT DOCUMENTS

CN        105659238         6/2016
EP        2241986 A1       10/2010
(Continued)

OTHER PUBLICATIONS

"Information Rights Management," Wikipedia, the free encyclopedia, retrieved from http://en.wikipedia.org/w/index.php?title=Information-Rights-Management&oldid=563243995, Jul. 7, 2013, 2 pp.

(Continued)

*Primary Examiner* — Darren B Schwartz
(74) *Attorney, Agent, or Firm* — Medtronic, Inc.

(57) ABSTRACT

A patient data exchange system comprises at least one device. Each of the devices implements an interface. When a device in the patient data exchange system publishes patient data, the device generates a metadata envelope that encapsulates the patient data. The metadata envelope conforms to a schema that defines allowable metadata attributes of the metadata envelope. When a device in the patient data exchange system receives a metadata envelope that conforms to the schema, the device determines, based at least in part on a metadata attribute of the metadata envelope, a particular patient data handling policy to apply to patient data encapsulated by the metadata envelope. In some instances, the metadata attribute indicates that authorization is required from an authorization service to access the patient data encapsulated by the metadata envelope.

20 Claims, 11 Drawing Sheets

Related U.S. Application Data

(60) Provisional application No. 61/868,461, filed on Aug. 21, 2013.

(56) References Cited

U.S. PATENT DOCUMENTS

| | | | |
|---|---|---|---|
| 7,890,180 | B2 | 2/2011 | Quiles |
| 7,926,114 | B2 | 4/2011 | Neystadt |
| 7,978,848 | B2 | 7/2011 | Zhu |
| 8,244,640 | B2 | 8/2012 | Venkatachalam |
| 8,782,404 | B2 | 7/2014 | Lamb |
| 8,819,164 | B2 | 8/2014 | Abzarian |
| 2002/0004727 | A1* | 1/2002 | Knaus ............ G06F 19/3418 705/3 |
| 2002/0124177 | A1* | 9/2002 | Harper ............ G06F 21/6245 713/189 |
| 2002/0169637 | A1* | 11/2002 | Akers ............ G06F 19/3418 705/3 |
| 2002/0184517 | A1* | 12/2002 | Tadayon ............ G06F 21/10 726/27 |
| 2003/0037054 | A1* | 2/2003 | Dutta ............ G16H 10/60 |
| 2003/0074564 | A1* | 4/2003 | Peterson ............ G16H 10/60 713/182 |
| 2004/0088374 | A1 | 5/2004 | Webb |
| 2004/0167858 | A1 | 8/2004 | Erickson |
| 2005/0027871 | A1* | 2/2005 | Bradley ............ H04L 67/1061 709/227 |
| 2005/0182956 | A1* | 8/2005 | Ginter ............ G06F 21/10 713/193 |
| 2006/0259325 | A1* | 11/2006 | Patterson ............ G06Q 10/10 705/2 |
| 2006/0282903 | A1* | 12/2006 | Jung ............ G06F 21/6227 726/27 |
| 2007/0078677 | A1* | 4/2007 | Hofstetter ............ G06F 19/322 705/2 |
| 2007/0101418 | A1* | 5/2007 | Wood ............ G06F 21/31 726/8 |
| 2007/0204078 | A1* | 8/2007 | Boccon-Gibod ....... G06F 21/10 710/54 |
| 2007/0240203 | A1 | 10/2007 | Beck |
| 2008/0097550 | A1 | 4/2008 | Dicks |
| 2009/0048644 | A1 | 2/2009 | Stahmann |
| 2010/0292556 | A1 | 11/2010 | Golden |
| 2010/0328320 | A1 | 12/2010 | Kerstna |
| 2012/0185267 | A1 | 7/2012 | Kamen |
| 2012/0203798 | A1 | 8/2012 | Gifford |
| 2012/0260346 | A1 | 10/2012 | Carey |
| 2012/0277543 | A1 | 11/2012 | Homchowdhury |
| 2013/0054467 | A1 | 2/2013 | Dala |
| 2013/0219462 | A1 | 8/2013 | Aratsu |
| 2014/0089008 | A1* | 3/2014 | Carner ............ G06Q 50/24 705/3 |
| 2014/0142963 | A1 | 5/2014 | Hill |
| 2014/0283059 | A1 | 9/2014 | Sambamurthy |

FOREIGN PATENT DOCUMENTS

| | | |
|---|---|---|
| EP | 3036668 | 6/2016 |
| WO | 2009023328 A1 | 2/2009 |
| WO | 2015027077 A1 | 2/2015 |

OTHER PUBLICATIONS

"Protect your documents from unauthorized viewing and sharing with FileOpen digital rights management solutions," Digital Rights Management, Document Security, FileOpen DRM Software, retrieved from www.fileopen.com, accessed Aug. 8, 2013, 1 pp.

Fred Wood, Diane Wold, Tom Guinter, Mary Lenzen, Gary Walker, Gail, Study Data Tabulation Model, W. Kubick, Ed., 2008. CDISC Submission Data Standards Team, 2008, p. 26.

Gartner 2012. CDISC-SDS Team, "STDMIG V3 1 2 Training Guide V3.8."

Gatsi et al., "Short-Range Wireless Technologies in the Healthcare Infrastructure of the Future," Athens Information Technology, Sep. 10, 2009, 87 pp.

Hartzog, W. 2012, "Chain-Link Confidentiality," Geogia Law Review, vol. No. 46, pp. 657-702, Dec. 4, 2012.

International Preliminary Report on Patentability from International Application No. PCTUS2014/052123, dated Nov. 19, 2015, 20 pp.

International Search Report and Written Opinion from International Application No. PCT/US2014/052123, dated Nov. 13, 2014, 8 pp.

Kamal et al., "A Telemedicine Application to Schedule Temperature in an In Vivo Sensor Network for Cancer Treatment," Telemedicine and e-Health, vol. 18 No. 10, Mary Ann Liebert Inc., Dec. 2012, 12 pages.

O. H. E. Congress, 2009. "American Recovery and Reinvestment Act of 2009," Sep. 30, 2009. http://www.gpo.gov/fdsys/pkg/BILLS-111hr1enr/pdf/BILLS-111 hr1enr.pdf.

Omer Ben-Shalom, Manish Dave, Toby Kohlenberg, Dennis Morgan, Stacy Purcell, Allen Ross, Timothy, Verrall, Terun Viswanathan, "Rethinking Information Security to Improve Business Agility," IT@Intel White Paper, vol. NA, No. NA, p. 8, Jan. 2011.

PwC Health Research Institute 2011, "Top health industry issues of 2012," Price Waterhouse Cooper, Nov. 2011.

Response to Second Written Opinion dated Jul. 9, 2015, from International Application No. PCT/US2014/052123, dated Sep. 9, 2015, 16 pp.

Response to Written Opinion dated Nov. 13, 2014, from International Application No. PCT/US2014/052123, filed on Jan. 23, 2015, 12 pp.

Rosenblatt, "Technology Comparison: Authentica Active Rights Management and Microsoft Windows Rights Management Services," Enterprise Digital Rights Management, GiantSteps Media Technology Strategies, Jul. 14, 2005, 24 pp.

Rozwell C. et al. 2006, "CDISC Standards Enable Reuse without Rework," Applied Clinical Trials, Jun. 2006, 76-78.

Second Written Opinion of International Application No. PCT/US2014/052123, dated Jul. 9, 2014, 6 pp.

T. E. I. U. L. 2011, "The future of healthcare in Europe", Economist Intelligence Unit, 2011.

U.S. Department of Health and Human Services 2014. Medical Device Data Systems, Medical Image Storage Devices, and Medical Image Communications: Draft Guidance for Industry and Food and Drug Administration Staff. www.fda.gov/MedicalDevices/ProductsandMedicalProcedures/GeneralHospitalDevicesandSupplies/MedicalDeviceDataSystems/default.htm.

US Department of Health and Human Services, US Food and Drug Administration (FDA) 2014, "Overview of Device Regulation,", Sep. 30, 2014.

"File Open Rights Manager," Cloud-based Document Rights Management, FileOpen Systems Inc., retrieved from www.fileopen.com/products/rightsmanager/, accessed on Aug. 8, 2013, 2013, 1 pp.

"FileOpen Solutions for Healthcare and Life Science," Healthcare & Life Science Solutions, Document Security, FileOpen, retrieved from www.fileopen.com/document-security-solutions/healthcare-life-science, accessed on Aug. 7, 2013, 1 pp.

* cited by examiner

| | | Public acceptance | Consumerization | Energy conservation consumption | Increased mobility | Technological progress | Growing healthcare costs | Total | Net | Tension |
|---|---|---|---|---|---|---|---|---|---|---|
| Energy/battery needs | | ++ | + | ++ | + | ++ | + | 9 | 9 | 0 |
| Electronics/sensors | | ++ | + | ++ | ++ | ++ | + | 10 | 10 | 0 |
| Bio-medical/composites | | 0 | + | 0 | 0 | ++ | + | 6 | 6 | 0 |
| Medical care | | ++ | + | + | + | ++ | - | 6 | 4 | 2 |
| Drug delivery | | ++ | + | + | ++ | ++ | + | 7 | 7 | 0 |
| Communication technologies | | ++ | ++ | +- | ++ | ++ | 0 | 8 | 8 | 0 |
| Information tech. (device data) | | ++ | ++ | +- | ++ | ++ | + | 11 | 9 | 2 |
| Strength (Sum Absolute Values) | | 12 | 8 | 9 | 8 | 14 | 6 | | | |
| Net (algebraic sum) | | 12 | 8 | 7 | 8 | 14 | 4 | | | |
| Tension (Strength − Abs. Val. of Net) | | 0 | 0 | 2 | 0 | 0 | 2 | | | |

Legend:
- ++ Strong positive interaction
- + Positive interaction
- 0 No interaction
- +- Positive and negative interaction
- - Negative interaction
- -- Strong negative interaction

FIG. 3

DATA DRIVEN SCHEMA FOR PATIENT DATA EXCHANGE SYSTEM

This application is a continuation of U.S. patent application Ser. No. 14/464,357, filed Aug. 20, 2014, which claims the benefit of U.S. Provisional Patent Application No. 61/868,461, filed Aug. 21, 2013, the entire content of which is incorporated herein by reference.

BACKGROUND

There are currently many heterogeneous systems for collecting, processing, and analyzing data associated with medical patients (i.e., patient data). Traditional information technology (IT) systems may be built to generate data, courier the data through defined secured channels, proprietary or otherwise, to an ecosystem of receivers for further processing, analysis, and exchange. These complex systems may be difficult to manage and maintain over their lifecycles. For instance, technologies may evolve and may be introduced into new ecosystems with uncertain consequences. Furthermore, these systems may be complex in part because of the varying and changeable regulations applicable to patient data. For instance, particular types of patient data cannot be shared with particular individuals or entities without particular types of consent from patients. Furthermore, such regulations may prescribe how patient data must be stored. At the same time, patients and researchers may want to be able to have access to patient data. For instance, patients may want to be able to access their medical records and search results on their mobile computing devices. Furthermore, only limited "security" is applied at the data layer today. For example, varying types of encryption (EAS, Blowfish, DES, etc.) and levels (AES where the key value may be 128 bit, 512 bit, etc.) at various points/components (e.g., the network, firewalls, gateways, storage devices) may exist as data traverses cyber systems, such as the Internet.

SUMMARY

This disclosure describes techniques that may simplify systems for collecting, processing, and analyzing patient data. The techniques of this disclosure may place metadata attributes on patient data via encapsulation. The metadata attributes may include security and privacy schema attributes. In other words, patient data may be encapsulated within a metadata envelope that has particular attributes specified by a schema. The metadata envelope may be specified by a system designer. The schema may indicate the allowable metadata attributes of the metadata envelope. The metadata envelope may be a set of data that logically encapsulates another set of data.

Encapsulating patient data in this way may make the patient data hardened, resilient, and more reliable on its own. The patient data may remain encapsulated within the metadata envelope even while "at rest" (i.e., while in storage). This may be in contrast to systems that add layers of security only as the patient data is transmitted through one or more computer networks (e.g., cyberspace). Encapsulation of patient data in a metadata envelope that conforms to such a schema may add an additional layer of security and privacy, as close to the patient data as is possible, adding protection and logic to ensure that the patient data is safe beyond its intended uses, even if the patient data is leaked outside secured systems in which the patient data was intended to remain.

The techniques of this disclosure may improve patient outcomes. In accordance with one or more example techniques of this disclosure, a data driven systems model made up of simple publisher-subscriber data exchanges built from a standard device data schema may be executed. The data driven systems model may include, as an example, native security and privacy attributes enabling a more secure, robust data exchange environment easily adaptable to emerging technologies, innovative products, and services.

Although the techniques of this disclosure are described with reference to patient data and are generally described with reference to a health care setting, the techniques of this disclosure are not necessarily so limited. Rather, the techniques of this disclosure may be applicable to other types of data and in other types of settings, such as governmental data, military data, industrial data, commercial data, and so on.

In one aspect, this disclosure describes a system for exchanging patient data. The system comprises at least one device that implements an interface. When the interface receives a metadata envelope that conforms to a schema that defines each allowable metadata attribute of the metadata envelope, the interface determines, based at least in part on a first metadata attribute of the received metadata envelope, a particular patient data handling policy from among a plurality of available patient data handling policies that the interface is configured to apply. Each of the available patient data handling policies prescribes a different way of handling patient data. In addition, the interface applies the particular patient data handling policy with regard to a particular set of patient data encapsulated within the received metadata envelope. When the particular patient data handling policy indicates that receiving authorization is required in order to access the particular set of patient data, the interface requests, to receive from an authorization service identified by a second metadata attribute of the received metadata envelope, the authorization to access the particular set of patient data.

In another aspect, this disclosure describes a method of handling patient data. The method comprises receiving, at an interface implemented by a device, a metadata envelope that encapsulates a particular set of patient data associated with a patient. The metadata envelope conforms to a schema that defines each allowable metadata attribute of the metadata envelope. The method also comprises determining, by the interface, based at least in part on a first metadata attribute of the received metadata envelope, a particular patient data handling policy from among a plurality of available patient data handling policies that the interface is configured to apply. Each of the available patient data handling policies prescribes a different way of handling patient data. Furthermore, the method comprises applying, by the interface, the particular patient data handling policy with regard to the particular set of patient data. The method also comprises, when the particular patient data handling policy indicates receiving authorization is required in order to access the particular set of patient data, requesting, by the interface, from an authorization service identified by a second metadata attribute of the received metadata envelope, authorization to access the particular set of patient data.

In another aspect, this disclosure describes a computer-readable data storage medium (e.g., a non-transitory computer-readable data storage medium) having instructions stored thereon that, when executed, configure an interface implemented by a device to receive a metadata envelope that encapsulates a particular set of patient data associated with a patient. The metadata envelope conforms to a schema that defines each allowable metadata attribute of the metadata envelope; determine based at least in part on a first metadata attribute of the received metadata envelope, a particular patient data handling policy from among a plurality of available patient data handling policies that the interface is configured to apply. Each of the available patient data handling policies prescribes a different way of handling patient data. The instructions also configure the interface to apply the particular patient data handling policy with regard to the particular set of patient data. The instructions configure the interface such that, when the particular patient data handling policy indicates receiving authorization is required in order to access the particular set of patient data, the interface requests, to receive from an authorization service identified by a second metadata attribute of the received metadata envelope, the authorization to access the particular set of patient data.

The details of one or more examples of the techniques are set forth in the accompanying drawings and the description below. Other features, objects, and advantages of the techniques will be apparent from the description, drawings, and claims.

BRIEF DESCRIPTION OF DRAWINGS

FIG. 3 is an example trend coupling matrix.

DETAILED DESCRIPTION

Figure 1:
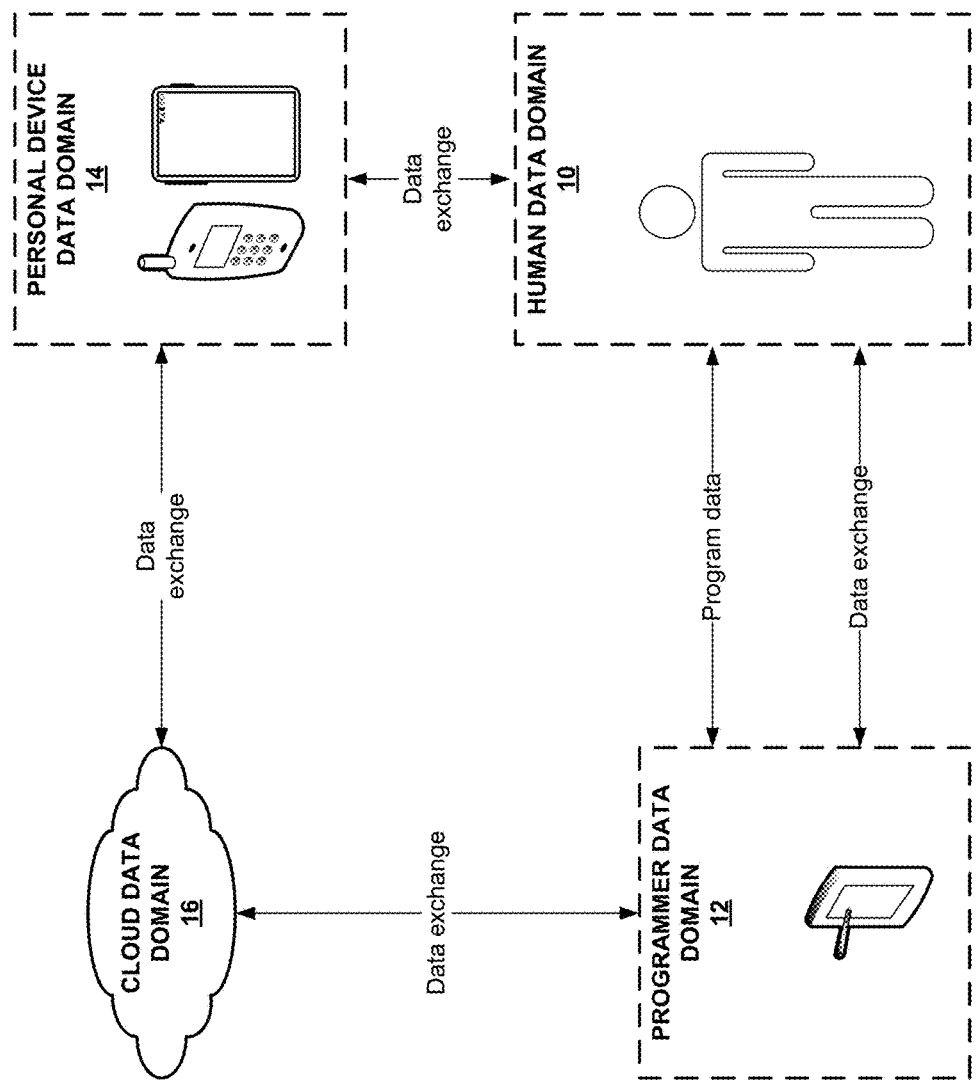
FIG. 1 is a conceptual diagram that illustrates an example device data exchange environment, in accordance with one or more techniques of this disclosure.

A patient data exchange system may comprise at least one device (e.g., a plurality of devices). The devices in the patient data exchange system may include implantable medical devices, device programmers for implantable medical devices (i.e., programmer devices), personal computers, mobile computing devices, server computing devices, and/or other types of computing devices. The devices in the patient data exchange system may exchange patient data. Such patient data may include data regarding patients. For example, the patient data may include clinical study data collected from a patient. In another example, the patient data may include an electronic medical record or an electronic health record. In another example, the patient data may include insurance records regarding a patient. In yet another example, the patient data may include prescription medication data regarding a patient.

Each of the devices in the patient data exchange system may act as a publisher and/or a subscriber. Each device in the patient data exchange system that acts as a publisher may implement a publisher interface. Each device in the patient data exchange system that acts as a subscriber may implement a subscriber interface. In this context, an "interface" may be a hardware and/or software structure that may act as a point of interaction between software and/or hardware.

When a device acts as a publisher, the device may receive, store, and/or generate data that is to be protected (i.e., protected data). The protected data may be encrypted and may include patient data. Furthermore, when a device is preparing to transmit the protected information, the publisher interface implemented by the device may generate a metadata envelope that encapsulates the protected data. In some examples where the protected data includes patient data, the patient data encapsulated by a metadata envelope may relate to, or may be based on, one or more patients. In some examples, the patient data comprises clinical study data, such as data generated in a clinical study. The metadata envelope may comprise metadata that is associated with the protected data. The publisher interface may transmit or store the metadata envelope. A subscriber interface of a device in the patient data exchange system may receive metadata envelopes that encapsulate protected data. In some examples, the subscriber interface may be a plug-in or extension for an existing software application, such as a web browser application or a PDF reader.

The metadata envelope may conform to a schema. In other words, the schema may define a format of the content of the metadata envelope. The schema may indicate allowable metadata attributes of the metadata envelope. In other words, a metadata attribute is an allowable metadata attribute if the schema indicates that the metadata attribute is allowable. A metadata envelope that conforms to the schema cannot include metadata attributes that are not allowed by the schema. For instance, the schema may require the metadata envelope to include various attributes. Each of the metadata attributes may comprise a particular type of data. In accordance with one or more techniques of this disclosure, the metadata attributes of the metadata envelope may specify how the protected data encapsulated by the metadata envelope is to be treated. When a subscriber interface receives a metadata envelope that conforms to the schema, the subscriber interface may determine, based at least in part on a metadata attribute of the metadata envelope, how to handle protected data encapsulated by the metadata envelope. For example, a metadata attribute of a metadata envelope may indicate a particular patient data handling policy to apply to patient data encapsulated by the metadata envelope. Hence, in accordance with one or more techniques of this disclosure, the patient data may be a declarative piece of data that one or more policies can be executed/acted upon based on the schema attributes. The patient data handling policy may be a policy that dictates a manner in which patient data is to be handled. In this example, a subscriber interface may determine the particular patient data handling policy based on the metadata attribute and may apply the particular patient data handling policy with regard to the patient data encapsulated by the metadata envelope.

For example, a metadata attribute of a metadata envelope may specify that patient data encapsulated by a metadata envelope is to be handled according to a particular policy (e.g., a governmental regulation, an organization-specific rule, an industry standard, etc.). In other words, the metadata attribute may indicate a governmental regulation applicable to the particular set of patient data. In some examples, the metadata attribute may indicate an identifier (e.g., an index) of the applicable governmental regulation. In this example, a subscriber interface that receives the metadata envelope may process and/or store the patient data encapsulated by the metadata envelope in accordance with the particular policy. Example governmental regulations applicable to patient data include regulations associated with the U.S. Health Insurance Portability and Accountability Act (HIPAA). In another example, a metadata attribute may specify that the patient data encapsulated by a metadata envelope belongs to a particular class. In this example, a particular policy may apply to patient data belonging to the particular class. In this example, a subscriber interface may process and/or store the patient data in accordance with the particular policy. Furthermore, in this example, if the particular policy is updated, the subscriber interface may be modified, without modifying the patient data or its metadata envelope, such that the subscriber interface processes and/or stores the patient data in accordance with the updated policy.

In one example, a subscriber interface may receive a metadata envelope that encapsulates a particular set of patient data associated with a patient. The metadata envelope may conform to a schema that defines each allowable metadata attribute of the metadata envelope. Furthermore, in this example, the subscriber interface may determine, based at least in part on a first metadata attribute of the received metadata envelope, a particular patient data handling policy from among a plurality of available patient data handling policies that the interface is configured to apply. Each of the available patient data handling policies may prescribe a different way of handling patient data. In this example, the subscriber interface may apply the particular patient data handling policy with regard to the particular set of patient data.

When the particular patient data handling policy indicates that authorization is required in order to access the particular set of patient data, the subscriber interface may request, from an authorization service identified by a second metadata attribute of the received metadata envelope, authorization to access the particular set of patient data. In this context, authorization may be an act of confirming that an entity that is seeking to access the particular set of patient data is authorized to access the particular set of patient data. In some examples, the authorization service only provides authorization to access the particular set of patient data when the interface provides evidence to the authorization service that the interface is configured such that the interface does not transmit the particular set of patient data in encrypted or unencrypted form outside the metadata envelope and does not generate copies of the particular set of patient data in unencrypted form that persist after termination of the interface. In other words, the interface receives the authorization to access the particular set of patient data only when the interface provides evidence to the authorization service that the interface is configured such that the interface does not transmit the particular set of patient data in encrypted or unencrypted form outside the metadata envelope and does not generate copies of the particular set of patient data in unencrypted form that persist after termination of the interface. In some examples, a remote computing device provides the authorization service. In some such examples, the subscriber interface may send a request to the authorization service via one or more communication networks, such as the Internet. In other examples, a unit of the computing device implementing the subscriber interface provides the authorization service.

In another example, the schema may specify that the metadata envelope is allowed to include a security attribute that identifies an authorization service. In this example, the authorization service may provide, to subscriber interfaces authorized to access the protected data, decryption keys for the protected data. An authorized subscriber interface may use a decryption key for the protected data to decrypt the protected data. Furthermore, in this example, the authorization service may only provide the decryption key to a subscriber interface if the authorization service is able to validate that the subscriber interface meets particular criteria. The authorization service may determine whether the subscriber interface is trusted software. Furthermore, in this example, the authorization service may track authorization requests.

In some examples, the authorization service may only provide access to the patient data (e.g., provide a decryption key) to a subscriber interface if the subscriber interface satisfies a requirement that the subscriber interface does not transmit the protected data in encrypted or unencrypted form outside the metadata envelope and does not generate copies of the protected data in unencrypted form that persist after termination of the subscriber interface. In this example, the authorization service may require evidence that the subscriber interface satisfies this requirement. In some such examples, the evidence may comprise authorization data encrypted according to an encryption key. In such examples, a requirement to receive the decryption key for the particular set of patient data to the interface from the authorization service may be that the authorization service is able to successfully decrypt the authorization data.

In another example, the protected data may include patient data and the schema may specify that the metadata envelope is allowed to include a privacy attribute that provides information about a consent given by a patient to share the patient data. For instance, the metadata attribute may indicate a type of consent given by a patient regarding sharing of the particular set of patient data. In another example, the metadata attribute may indicate a country in which consent was given by a patient regarding sharing of the particular set of patient data. In this example, if a publisher interface receives a request for the patient data, the publisher interface may determine, based at least in part on the privacy attribute, whether to provide the metadata envelope in response to the request. Similarly, if a subscriber interface receives a metadata envelope, the subscriber interface may determine, based on the privacy attribute, whether to accept the metadata envelope. If the subscriber interface does not accept the metadata envelope, the subscriber interface may delete the metadata envelope and the protected data encapsulated by the metadata envelope. For example, the subscriber interface may determine, based on the particular patient data handling policy, whether to delete the particular set of patient data. In this example, the subscriber interface may delete, based on the determination, the particular set of patient data.

In this way, the manner in which each unit of protected data in the patient data exchange system is handled may be governed by the attributes of the metadata envelope that encapsulates the protected data. This may obviate the need for complex, heterogeneous systems for different types of patient data. Rather, all protected data may be handled by the same set of publisher interfaces and subscriber interfaces according to the attributes of the metadata envelopes that encapsulate the protected data. Thus, although different types of protected (or unprotected) data are handled differently in the patient data exchange system, publisher interfaces and subscriber interfaces may determine in the same way how to handle particular pieces of protected (or unprotected) data.

Furthermore, the publisher interfaces and subscriber interfaces may handle metadata envelopes that conform to different schemas. In some examples, the publisher interfaces and subscriber interfaces may exchange schemas to enable extension of types of metadata envelopes in the patient data exchange system.

As indicated above, many medical devices and their solutions are heterogeneous, coupled, and complex systems that collect, process, and analyze data from an implantable device so as to manage a patient's disease state via algorithms mapped to therapies. These solutions are regulated and controlled, in the U.S., by the Food and Drug Administration (FDA). As new information technologies (IT) emerge and are introduced into consumer markets, users may need ready access to digital data. Current systems may be built and designed around technologies to solve discrete health challenges, yet they are not designed with regard to the accessibility of the data that these technologies create, store, and/or share. An opportunity may exist to define a standard data schema for all implantable medical device data (or all implantable medical data from an enterprise or organization). The resulting standard may enable improved methods to share and exchange device data with other implantable medical devices and extend to external data domains hosted locally, regionally, or globally (e.g., electronic health record system, health information technologies, national healthcare systems, etc.). This standard may include a set of schema attributes focused on information security and privacy. This approach may form the basis for a data centric, secure publisher and subscriber systems model for health data exchanges to simplify current complex systems.

The proposed approach may leverage projects to define a sample data schema including security and privacy components. This may be important because:
  Clinical Businesses, due to the nature of clinical studies, are accustomed to working new solutions and are receptive to investigating new data proposals.
  Clinical data is housed in IT systems today and interoperates with other systems.
  Clinical data is used to help with FDA submissions.
  Clinical data is used for quality and assurance.

This approach may afford a real world exercise. After a system model is mapped and shared with other experts in the clinical domain, a mind mapping of data flows and systems integration may be created. These models may be used to better understand where and how a data schema standard can be scrutinized and scrubbed across changing policy domains. That is, the system solution may not need to be modified or redesigned to support a policy change with regard to the access, exchange, or usage of the data being described. Instead, changing a policy engine within the system may make the policy engine compliant with modified or newly defined regulations.

In this disclosure, a model for exchanging device data is developed and demonstrated, throughout a healthcare ecosystem, using a publisher-subscriber systems model. This model may be advanced by the creation and execution of a standard data schema that encapsulates content making the model more resilient and secure. This effort may lay the foundations for many other data driven, domain specific, schemas for the seamless and secure access of data within complex "just in time" systems.

Information technologies are advancing. As a result, consumers may become further engaged in building personal solutions made up of composite applications, systems, and devices to support the exchange of information (e.g. financial, personal, social, medical, etc.) to improve their lives. An organization may consider how its devices (specifically the valuable data they generate) play a part in this improved automation and data processing/analytics environment. In some examples, one possible interpretation of the organization's role is as follows:

Vision—Evolve legacy complex systems into a simple, secure, and efficient structure using a publisher-subscriber model. Medical devices and traditional information technology (IT) systems may converge. For example, medical devices, including sensors and telemetry, are maturing and producing information (data) that has the potential to lower healthcare costs, deliver higher quality care, and be data mined to provide healthcare systems feedback and analysis to improve patient outcomes.

Goal—Standardize medical device data with a standard schema having native security and privacy attributes. This standardization may form a foundation to make simple building blocks composed of basic publisher and subscriber systems model for information exchanges. The scope and results of this disclosure may demonstrate vision feasibility and investigate alternatives.

Why—The publisher-subscriber model may be a simple system that can be extended to build more complex data exchange models and ultimately improve a decision maker's ability to balance risk and reward. The flow of critical data may enable the correct information systems to analyze, measure, and respond with the highest quality and value. In addition, this analysis may identify gaps, provide next steps, and suggest options on how to gather more data and refine measurements to determine metrics for improved outcomes.

How—Conduct feasibility testing with a clinical project to standardize data for FDA submissions and include security and privacy, which may not be a primary intention of the clinical project, to improve data exchange controls. Experience gained may reinforce the vision mentioned above and/or identify other opportunities for reducing complexity of healthcare data exchange to improve patient outcomes.

The techniques of this disclosure may prepare organizations to re-evaluate their roles from a medical device manufacturer only, to data authority, publishing critical and valued information for a global health care ecosystem. More specifically, one or more technique of this disclosure may define a standard data centric set of device data schema for all its devices (sensors and telemetry). In some examples, one or more techniques of this disclosure may suggest a data schema and demonstrate feasibility of an efficient, secure, and highly exchangeable data environment encompassing local, regional, and global Health Information Systems (HIS), such as illustrated by FIG. 1.

FIG. 1 is a conceptual diagram that illustrates an example device data exchange environment, in accordance with one or more techniques of this disclosure. In the example of FIG. 1, there are four distinct data domains in which data is created and/or modified, exchanged, or stored. These domains include a human data domain 10, a programmer data domain 12, a personal device data domain 14, and a cloud data domain 16. Each of these domains may, itself, be a conceptual model of complex systems made up of many digital components (e.g. computing endpoints, servers, operating systems, databases, networking equipment, standard protocols, etc.). In some examples, each of these high-level domains may be a publisher and/or subscriber of data from one domain to another. Devices in each of these domains may implement the publisher and/or subscriber interfaces of this disclosure.

Human data domain 10 may comprise the traditional location of implantable/wearable devices (e.g., pacemakers, insulin pumps, sensors, drug pumps, neurostimulators, etc.) that generate, record, and act on data sensed from patients. This data (i.e., device data) may be critical to algorithms used to manage and improve a patient's quality of life by providing improved therapies throughout the lifecycles of diseases. This device data may be critical, sensitive, and during a clinical trial valued information, such as during a controlled scientific study to prove the efficacy and safety of a new product/therapy/technology being introduced for a regulating entity's approval for human use—e.g., by an FDA regulatory approval board. The value of the device data may imply a need to ensure integrity, confidentiality, and availability of the device data. Today, this data and corresponding disease state it is managing may be a monolithic data set that does not interface with other human data domain devices (e.g., a pacemaker that shares information with an insulin pump). Although FIG. 1 shows a human, the human does not form a part of the techniques of this disclosure.

A standard data schema, outlined later in this document, may enable new data exchanges within the body from device to device. For example, this communication channel may improve therapy reaction times, early identification of co-morbidity states, and reduce patient hospital visits.

Programmer data domain 12 may comprise a controller that uses a proprietary communications link to create a secure channel to the implantable device for the purpose of maintenance, management, and data acquisition. As shown in the example of FIG. 1, devices in programmer data domain 12 may send program data to devices in human data domain 10. The program data may comprise data to program devices in human data domain 10. Furthermore, as shown in the example of FIG. 1, devices in programmer data domain 12 may exchange, via publisher and subscriber interfaces, data (e.g., health data, device data, etc.) with devices in human data domain 10 and cloud data domain 16. Standardizing on a data schema may enable a programmer model (e.g., a programmer for programming a medical device) designed with common off the shelf hardware running standard operating systems. For example, this hardware, and a hardened operating system of the hardware, may be used to host virtual machine solutions (similar to the hardware equivalent solutions used today, however, all software components may have been encapsulated into a virtualized layer). Such a solution may reduce programmer costs and may enable multiple programmer options.

Personal device data domain 14 may comprise the realm of consumer information technology product proliferation and the convergence of a patient's instant data access expectations. For instance, personal device data domain 14 may include mobile phones, personal computers, tablet computers, laptop computers, wearable computing devices, and other types of computing devices used by patients. In the example of FIG. 1, devices in personal device data domain 14 may also exchange, via publisher and subscriber interfaces, data with devices in human data domain 10 and devices in cloud data domain 16. That is, in some examples, a patient's belief that their medical information can be accessed, anytime, anywhere, and from any device they have access to or buy from consumer electronic providers may be realized. US Food and Drug Administration, "http://www.fda.gov/MedicalDevices/ProductsandMedicalProcedures/GeneralHospitalDevicesandSupplies/MedicalDeviceDataSystems/default.htm," U.S. Department of Health and Human Services, 19 04 2011. [Online], available from: http://www.fda.gov/MedicalDevices/ProductsandMedicalProcedures/GeneralHospitalDevicesandSupplies/MedicalDeviceDataSystems/default.htm, provides some guidance regarding these types of system components. However, it is the responsibility of the device manufacture to comply with these regulations. These regulations may be difficult to comply with in a controlled and well managed environment versus a new, dynamic, environment with little control of personal devices. A standard data schema model may provide an opportunity to build just in time systems, where interfaces can control data flow that is auditable, secure, and compliant with today's regulations and devices. In addition, this modularity may make the systems more resilient to changes in the future.

Cloud data domain 16 may comprise the traditional Internet of resources, data repositories, services providers (e.g., insurers, personal health records, hospital electronic medical records, payers, etc.) and applications that interface and exchange data generated by devices. As shown in the example of FIG. 1, devices in cloud data domain 16 may exchange, via publisher and subscriber interfaces, data (e.g., health data) with devices in programmer data domain 12 and devices in personal device data domain 14. This may be further refined by network controls that zone the cloud data domain into three types: local Intranet (on premise only data exchanges), regional Intranet (private only data exchanges that span geo-locations and political boundaries), and the Internet itself.

A standard data schema model may provide layers of information (encapsulation) that provide additional context, like privacy and security, as close to the data source as possible. The result of this encapsulation may be data hardening, resiliency, and reliability of the data being exchanged. To support this, a different methodology using a publisher-subscriber model further simplifies the complexity of the device data exchanges. This methodology may be enabled by the creation of taxonomy, a schema adding context to data being exchanged from a publisher to a subscriber. Traditional systems may be built to generate data, courier the data through defined secured channels, proprietary or otherwise, to an ecosystem of receivers for further processing, analysis, and exchange. This may be difficult to manage and maintain over the lifecycle of the defined system and its components (i.e. technologies may evolve and be introduced into ecosystems with uncertain consequences). In addition, the only "security" placed on data is encryption of varying types (EAS, Blowfish, DES, etc.) and levels (AES the key value may be 128 bit, 512 bit, etc.) at various points/components (e.g. the network, firewalls, gateways, storage devices, etc.) as the data traverses these systems.

The techniques of this disclosure may place content attributes (e.g., security and privacy attributes) via encapsulation on the data (e.g., protected data) to make the data hardened, resilient, and more reliable on its own instead of systems being built to add layers of security on the data's journeys in cyberspace. This data schema may add an additional layer of security, again as close to the data as possible, adding protection at the data level to ensure the data is safe beyond the data's intended uses, if leaked An example purpose of the project is to leverage a defined industry standard data model for all clinical trials to improve the FDA submissions processes. Gartner, Inc., an IT research and advisory group, published a paper outlining cost savings and corresponding areas in clinical trials where data standardization may streamline activities for FDA submissions. Gartner's suggestion was the use of Clinical Data Interchange Standards Consortium, Inc.'s (CDISC) Study Data Tabulation Model (SDTM) version 1.2.

TABLE 1

"Clinical Study Activities Streamlined with CDISC standards" exhibits process areas that benefit from data schema standardization of clinical record data exchange, storage, analysis, etc.

| Study startup | Study conduct | Analysis/Reporting | Submission |
|---|---|---|---|
| Study design | Patient recruitment | Data analysis | ISS/ISE preparation |
| Protocol development | Data exchange | Safety assessment | Clinical-statistical |
| CRF development | SD verification | Analysis table | integrated report |
| DB structure/validation | Site monitoring/audits | preparation | Listings, tabulations |
| Edit checks/validation | Transfer of lab/ECG data | Clinical assessments | and datasets |
| LAB/ECG Specs | Site audits | Report generation | eCTD fils structure modules (2-5) |
| Site/PI identification | Database QA and Lock | | |
| Site evaluation | Analysis programming | | |
| Site initiation | Initial stat tables | | |
| Patient recruitment plan | Study closeout/archive | | |
| Critical documents | | | |
| IRB approvals | | | |
| Training of teams/sites | | | |
| Randomization plan | | | |
| Test article prep | | | |
| Statistical analysis plan | | | |
| Analysis table shells | | | | outside secured systems within which the data was intended to remain. As data exchanges from each publisher-subscriber interfaces (e.g. software or hardware policy engines) make decisions to add additional layers of defense, more encapsulation around the content to be shared, and the resulting data model may be conceptually similar to that of Russian dolls.

The following portion of this disclosure describes example tools used and results assembled from these methods to demonstrate that an organization embraces information technologies with a device data driven strategy to define a standard data schema for all the organization's devices and solutions. This goal may support a vision of an ecosystem made of simple data exchanges between publishers and subscribers, thereby reducing data flow complexities and challenges with numerous regulatory and compliances. The results may be better patient outcomes due to the exchange of high valued device data throughout the healthcare's information technology's ecosystems.

To achieve a simple, secure, and efficient health care ecosystem, having discrete publishers and subscribers collaborating and exchanging data, a common shared data standard may be defined. Clinical business leaders identified in an internal clinical data standardization project may be targeted to investigate such a schema standard. The clinical business and clinical studies may be accustomed to looking at new solutions, the challenges they introduce, and may be receptive to the investigation of this proposed new data strategy. In addition, the data maintained by clinical teams may be already warehoused in global IT solutions.

In Table 1, italicized text indicates clinical study activities that may be streamlined with standards. From Gartner's research, the majority of cost savings, including improved FDA submissions, are process enhancements which equated to the reduction of eight months of clinical study efforts.

Figure 2:
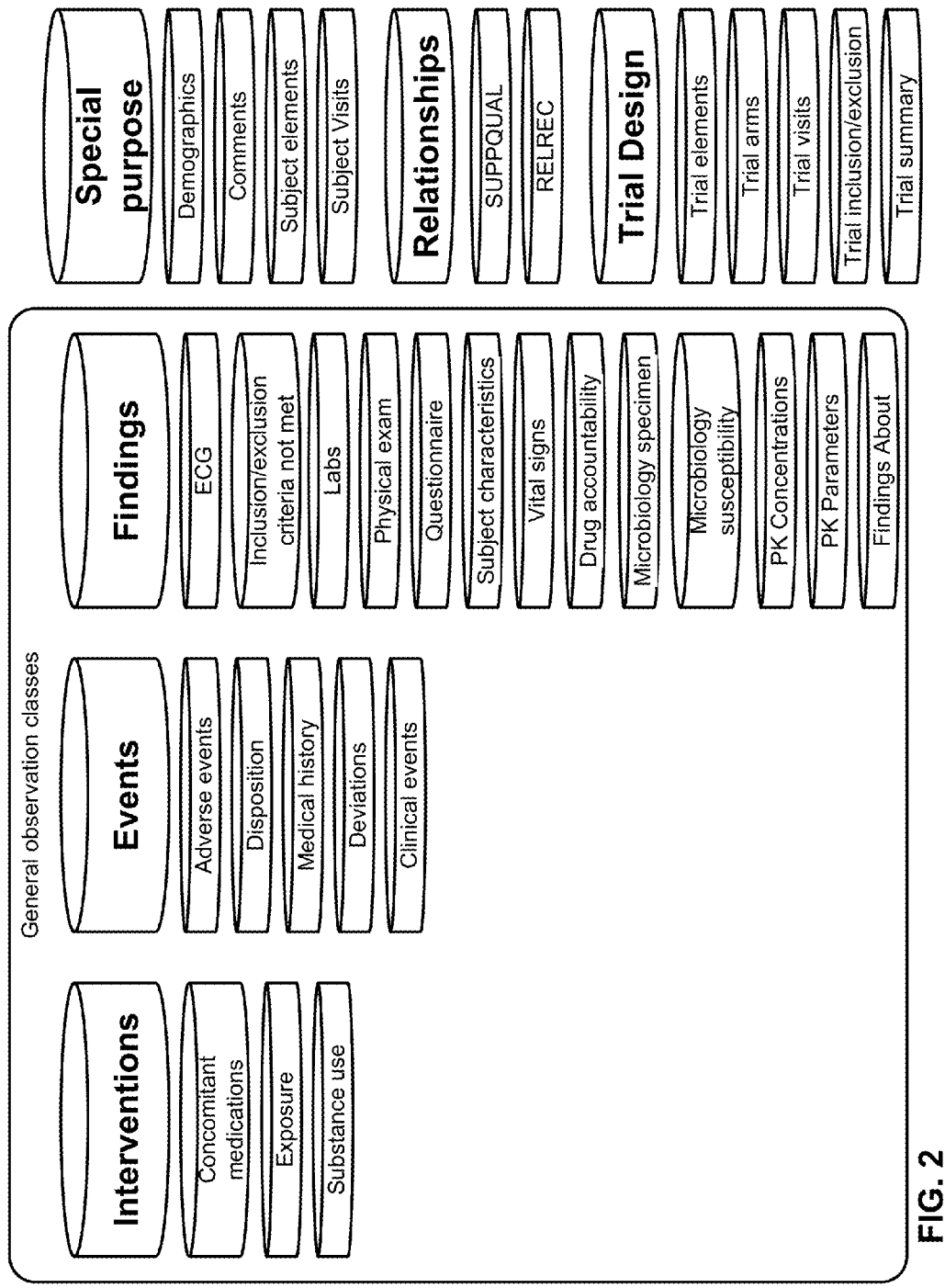
FIG. 2 is an example logical depiction of the Clinical Data Standards Consortium's Study Data Tabulation Model.

FIG. 2 is an example logical depiction of the CDISC SDTM. The SDTM data model is based upon clinical study records, where each record represents the subject (i.e., the participant/patient) observations, and includes the following components schema hierarchy:

Classes—six top level groups that define the study.
Domains—sub categories of classes that provide standard details of the subject within the study.
Variables—attribute roles that hold the detail data gathered in the study observations.

An important, but unfortunate, observation is that there is no privacy or security built into this model. However, the SDTM has built into it a method to extend the standard, for industries requiring further enhancements, via the special purpose class. To improve the quality, integrity, and value of the clinical data, the SDTM schema was extended to include two new domains. Privacy and security domains were included via the special purpose class and contained new variables and attributes, which are described later in this disclosure.

An approach to leverage one or more techniques of this disclosure throughout an organization is twofold:

1. A clinical portion of an organization may consume clinical data into a data warehouse, but using a new data model. This data flow may comprise the simple publisher-subscriber model proposed as a long term vision for simplifying complex systems. The data warehouse may comprise a hub where data can be exchanged with other internal systems or external systems for further processing (e.g. FDA submissions, Electronic Health Record systems, etc.).

2. The consumption of the clinical data using the SDTM may already be based on industry standards like extensible markup language (XML) and placed into a well-defined data warehouse system.

This leverage may translate into a simple low risk opportunity to gain knowledge and feasibility on proposed concepts. If the project for the organization presents any negative impact to the original project goals, then the project can easily be shelved and the proposed security and privacy additions can be revisited at a more appropriate time.

It may be important to define a standard data schema (e.g., define a taxonomy of standard attributes to describe the content generated, stored, and shared) for all device data.

This is because security of data and exchange of the data may be paramount for ensuring quality, safety, and building a foundation for future innovation using the data. As the trends presented above unfold, device data may be subject to the five laws of data, stated by Intel's Chief Information Security Officer Malcolm Hawkins:

1. Information wants to be free: People are social and will talk, post, and share information. Consumerization of information technologies will only increase this risk.
2. Code wants to be wrong: There is no such thing as 100% error-free software or firmware controlling hardware.
3. Services want to be on: Always on and connected means that there are processes and code constantly running and can be exploited by attackers, process mistakes or misconfigurations during required changes.
4. Users want to click: People naturally trust and are lead to activities that are malicious, innocent, or benevolent by clicking buttons, web links, or any message box prompts.
5. Even a security feature can be used for harm: Security tools, processes, and policies can be exploited just like software and hardware. This means that laws 2, 3, and 4 above are also true for security measures at various layers of defense.

What appears to be constant is the exchange of information between users, applications, and systems that are built to herd and shepherd data within complex digital systems. To improve the controlled exchange of information from container to container controls on the data being transferred may be applied. That is, security (or other controls like privacy) may be "baked into" the design of information technologies data exchanges, at the data level. Discrete publisher-subscriber systems built to exchange device data "metadata standards" may be able to apply new policies, refine controls, and provide granular logs at their interfaces to help reduce the impacts to the threats above.

The evolution from status quo to a data authority (i.e. a data publisher in an ecosystem of subscribers) may begin by implementing a defined device data schema for improved data exchanges. Using new tools like the Trend Coupling Matrix, Idea Mapping, and Technology Space Mapping, may work to re-enforce the need for a device data classification standard for better internal data exchanges which may also benefit customers and improve patient outcomes as the data is shared outside systems.

FIG. 3 is an example trend coupling matrix. Listed across the top row are mega-trends that may or may not upset the advancement of technologies (those listed in the first column) that an organization may implement today. The trend coupling matrix may demonstrate and highlight the impact of information technologies (device data) on the global healthcare ecosystem within which an organization's medical devices and services participate. More specifically, the trend coupling matrix may demonstrate and highlight how the organization's device data seamlessly, securely, and with privacy concerns addressed, exchange with other IT systems (e.g., consumerization, healthcare systems, mobility, and advancing technologies).

In the example of FIG. 3, Information Technologies (device data) may be a compelling technology and may be pursued within the strategies across all devices that collect, store, or transmit data for further processing and/or decision making. A result of this exercise was the reinforcement of concerns related to the additional energy consumption in order to store, transmit, and maintain constant connectivity (i.e. increased mobility) to the Internet for sending/receiving device data. Further downstream effects of implementing Information Technologies (device data) standards, may result in prolonging the life of its users and have the potential of adding to the total costs of healthcare. However, the net result of Information Technologies (device data) on other healthcare related savings (e.g. inventory management, return visits, emergency room visits) may result in a net improvement in savings.

Figure 4:
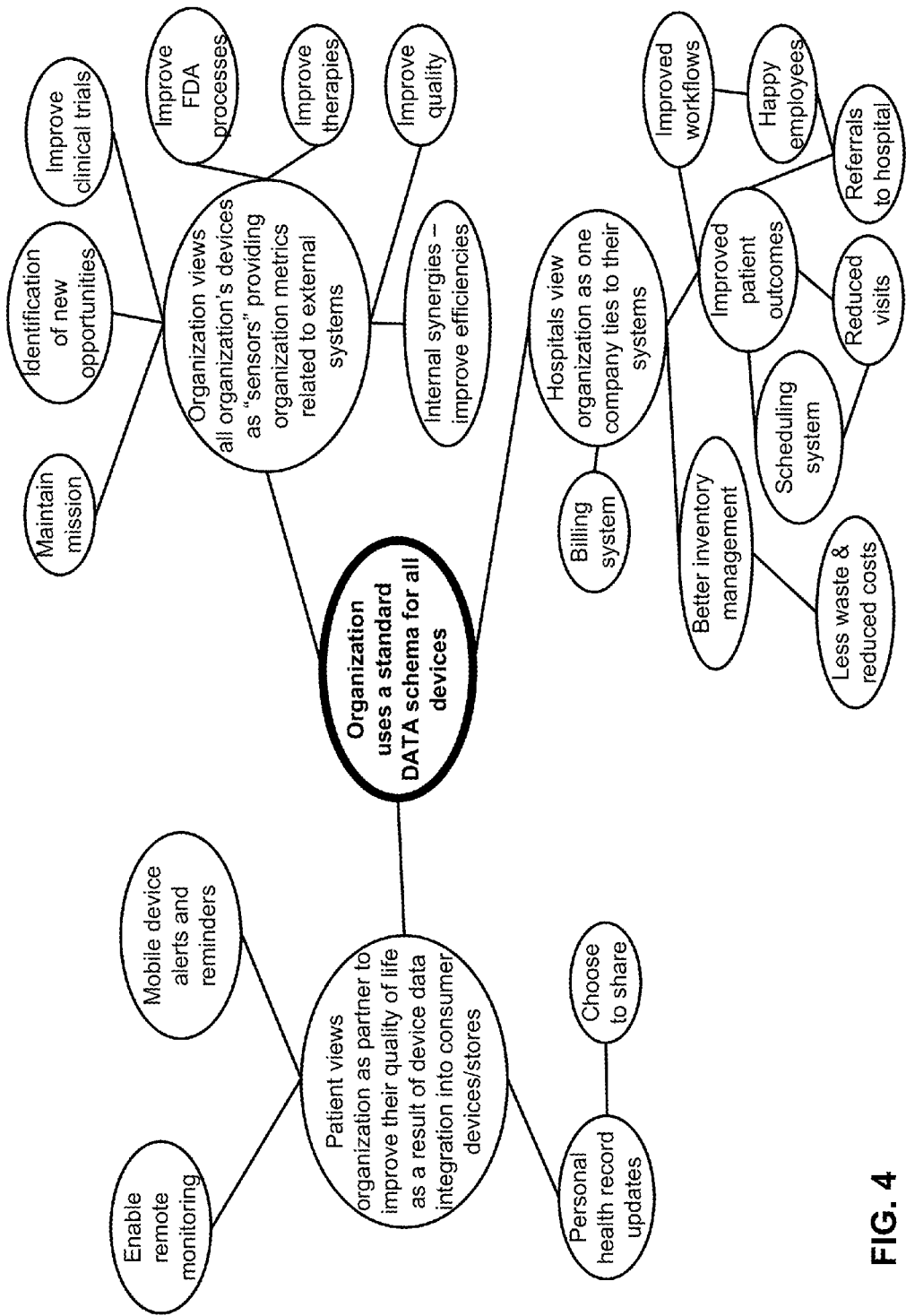
FIG. 4 is an example "Idea Mapping" that lists key stakeholders and conceptual benefits of using Information Technologies (device data).

FIG. 4 is an example "Idea Mapping" that lists key stakeholders and conceptual benefits of using Information Technologies (device data). These stakeholders (i.e. patients, providers, and payers) and the optimistic benefits outlined may be weighed against the uncertainties discussed later in this section. However, this may be a start for further refinement and detailed financial analysis.

Figure 5:
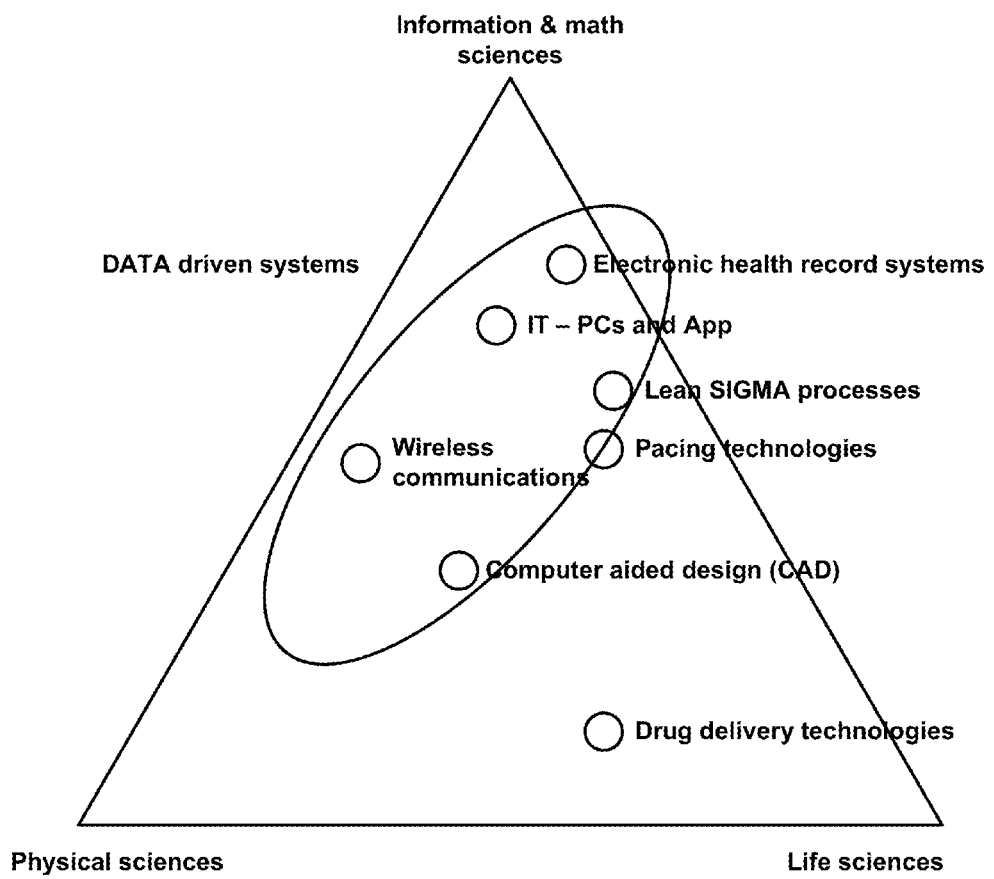
FIG. 5 is an example "snap shot" of key technologies/solutions that may already be in place at an organization and positions of the key technologies/solutions within the organization.

FIG. 5 is an example "snap shot" of key technologies/solutions that may already be in place at an organization and positions of the key technologies/solutions within an organization. In this organization, it appears there is a trend toward Information and Math Sciences within the tools used to support the organization's core businesses and the traditional corporate IT businesses. That is, data used and shared by internal IT organizations may be leveraged to improve the processes and tools used in device manufacturing/life sciences solutions to reduce costs, improve quality, and improve the speed to market for new products (recall the clinical example provided). As the organization's businesses mature, consumerization and commercialization of IT systems may continue. The Internet may become more pervasive with greater reliance on data exchanges, and the organization's device data (e.g. device "sensors") may become increasingly critical to improved efficiencies, insight, and further advancements of technologies and products. If data can be stored, transferred, and presented in a standard, seamless, and trusted way within the organization's IT systems, the data can be extended to external systems—e.g. health IT systems.

The resulting data standard (i.e. a defined device schema) may enable improved methods to share and exchange this data with other implantable medical devices within the body, and create new therapy opportunities, external Health IT ecosystems, and still afford an organization the ability to control the data flow ensuring regulatory and compliance. Additional results may be proof of therapy compliance and co-morbidity detection from other device data coloration (to mention a few).

Information technology (device data) may be critical to the organization's mission outlined above. The tools have demonstrated the convergence of Information Technologies (device data) and its use in the organization's technologies and the synergies with industry trends. The previous sections may convey the benefits and rewards of implementing a standard device data schema. The following section of this disclosure provides additional considerations regarding the techniques of this disclosure.

The previous sections are very positive outcomes and consequences of implementing a standard schema for an organization's device data. However, the organization may need to address the following challenges, at a minimum, with the implementation of this new methodology—i.e. standard schema for device data:

- The need to develop new processes and requirements: today's procedures and device methodologies require changes, updates, and re-tooling.
- Regulatory and compliance—e.g. FDA ramifications or new processes for submission of products and their data flows. That is, will the organization be required to maintain more data for a longer period of time?
- As health technologies improve and are further capable as human sensors, the health technologies may be combined with other IT services like GPS for location monitoring and tracking of persons (e.g. a national or otherwise). Governments may take measures to ensure the data is properly used, controlled, and managed over its lifecycle.
- Generate plans and processes to ensure "worse case" scenarios are mitigated (e.g. what if metadata is compromised?).
- Does the organization publish/share an anonymous version or subset of this data for the greater good?
- The assumption is that this standard device data schema is adopted by the industry—CDISC has taken 13 years to mature and is not industry wide today. In addition, would this standard support the larger vision of a complex ecosystem of simple publisher-subscriber systems model adoption?

This is not an exhaustive list and an area that may be further refined by implementing the recommendations defined in later sections of this project.

Figure 6:
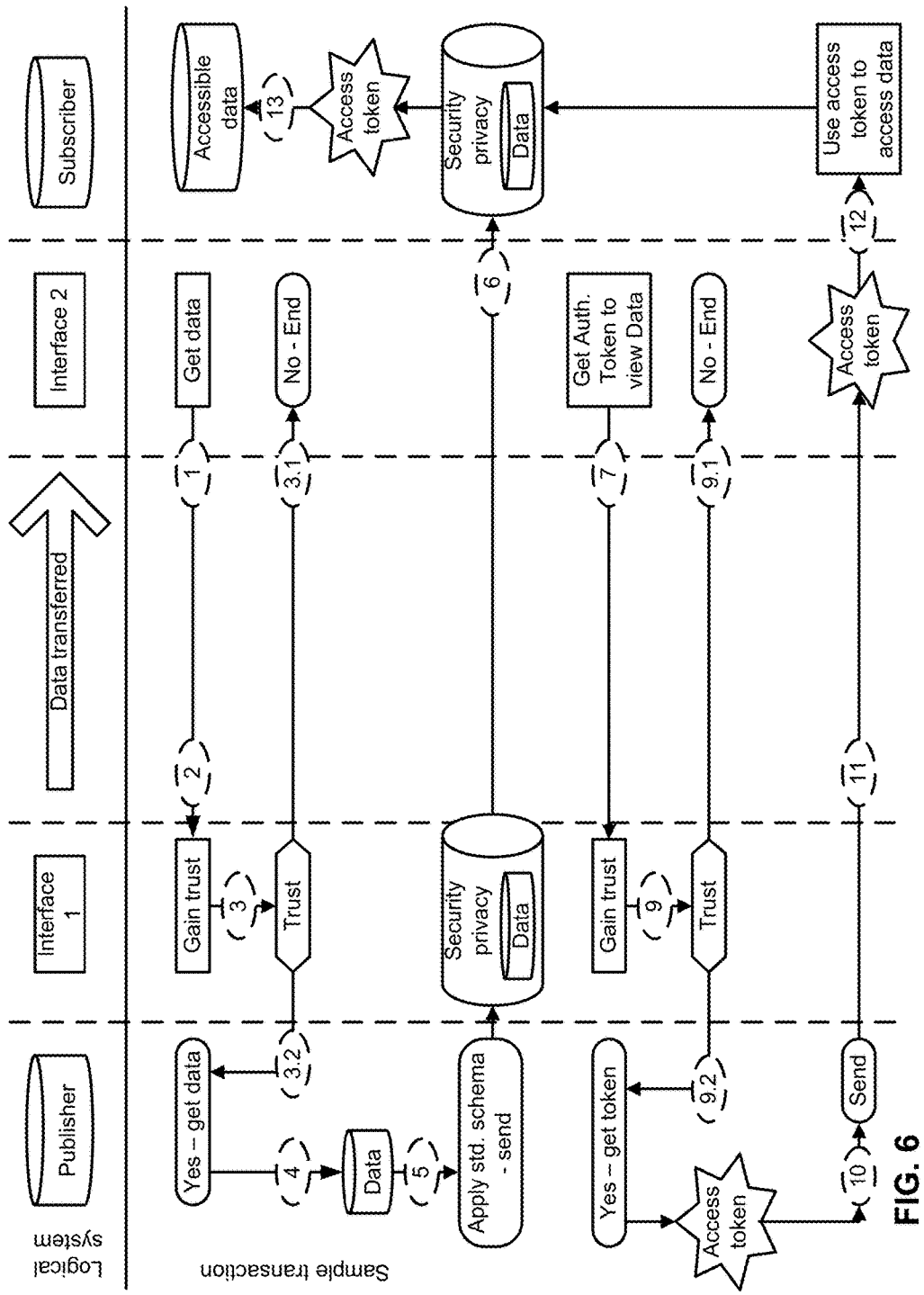
FIG. 6 illustrates an example logical system architecture of a publisher-subscriber model, and includes a sample data transaction/exchange between the two entities that encapsulates data with a standard schema.

FIG. 6 illustrates an example logical system architecture of a publisher-subscriber model, and includes a sample data transaction/exchange between the two entities that encapsulates data with a standard schema. The standard data schema illustration only demonstrates security and privacy key value pairs, outlined later in this section, but could include any set of attributes to be defined.

The publisher-subscriber model may be a foundational two party transactional data exchange system used to build higher ordered and more complex ecosystems. The interfaces (hardware or software) may be designed to understand, interpret, and execute functions depending on the data being exchanged. More specifically, the interfaces may comprise policy engines that gate data exchanges evaluated by the contextual metadata encapsulated in the shared information. This may translate into a more adaptive system because the interfaces add feedback to the higher order systems made of other publisher-subscriber components and driven by the data. Further, as data demands change or the ecosystem of publisher-subscriber components are impacted by disruptive technologies (e.g., new laws, regulations, intended data uses, malicious actors, or protocols and devices) the interfaces, or schema, are modified to meet these new challenges. Other portions of this document provide more detail on the components of this model.

FIG. 6 also outlines an example sequence of a simple transaction between a publisher and a subscriber. The model demonstrates the concept of data being shared, yet also protected at rest (i.e. in the publisher or subscriber container), in transit, and additional protections due to encapsulated metadata (i.e. the schema that creates a policy around the data that could describe more security and better privacy attributes). This encapsulation creates another layer of information that is tagged to the data and enforced beyond the original publishing authority. Additional details on the sequence of data exchanged between a publisher and subscriber illustrated in FIG. 6 are provided below.

Publisher—This system component is an authoritative source of data. The publisher can be, but is not limited to, any of the following:
- Device—e.g., computer, mobile phone, implantable hardware, sensor, etc. that generate content
- Storage container—e.g., hardware appliance that stores structured or unstructured blobs of content (e.g. database, file, or RAW) generated by a device
- Application—a piece of software that creates content by means of algorithms and procedures A human may be a publisher (author, owner, and creator) of data but for the purposes of this disclosure is not included as a discrete component. This is because the data/content of a human is transferred manually from the human to the publisher via a human interface device (e.g. keyboard, mouse, microphone, touch screen, sensor, etc.). This inclusion may change as new interfaces that transfer cognitive data directly into computing systems (e.g., cyberspace) mature.

Interface 1—This system component can be either a hardware or software entity that facilitates the requests for data from a subscriber. The interface includes the protocols used to request, read, interpret, log, and, via policy, gate the proper exchange (e.g. packaging and sending) of content to be sent to a subscriber. Interface 1 may be an instance of a publisher interface.

Data Transferred—This systems component may represent the various mediums used to carry out the transmission of digital content negotiated between a publisher and subscriber. Data can be transferred via Internet or Intranet networks (i.e. physical infrastructure like LAN/WAN via TCP/IP protocols), USB keys, CD/DVDROM, etc.

Interface 2—This system component can be either a hardware or software entity that facilitates the requests from the subscriber to a publisher. The interface includes the protocols used to get, read, interpret, log, and, via policy, gate the proper exchange (e.g. receipt and unpacking) of content from a publisher. Interface 2 may be an instance of a subscriber interface.

Subscriber—This system component is an entity requesting valued data from an authoritative source, a publisher. The subscriber can be, but is not limited to, any of the following:
- Device—e.g., computer, mobile phone, implantable hardware, sensor, etc. that generates content.
- Application—software that automates the request for content by means of algorithms and procedures.

A human can be a subscriber within this system model, but are not included in the techniques of this disclosure because human consumption of data is via traditional methods such as printouts, displays and video and audio formats. As technologies advance to provide information into the human brain directly, the monitoring of this data transfer may be left to physical access controls.

The following describes the sequence diagram of simple transactions, from FIG. 6, between a publisher and subscriber. The model demonstrates the concept of the data being shared, yet protected at rest and in transit, while data and encapsulated policy (e.g. security and privacy) are exchanged.

1. Get data—Subscriber requests data from publisher.
2. Gain trust—Interface 1 receives request.
3. Trust—Interface 1 establishes trust with the subscriber from standard authentication methods.
   3.1 No-End—if NOT trusted the transaction is terminated.
   3.2 Yes—get data—if trusted authorization to the data is made.
4. Data—the data is accessed and bundled.
5. Apply standard schema—send—the bundled data is encapsulated, with the defined schema, and sent to Interface 2 (subscriber).
6. The content is now in the subscriber's control, but may not be accessible until policy is met from the declaration of the standard schema. For example, in the illustration the schema requires an authorization token to decrypt the content to view data.
7. Get Authorization Token to view Data—when the subscriber mounts the content, it forces subscriber to get authorization token from the publisher (note this could be a $3^{rd}$ party identity provider).
8. Gain trust—Interface 1 receives request.
9. Trust—Interface 1 establishes trust with the subscriber from standard authentication methods.
   9.1 No-End—if NOT trusted the transaction is terminated.
   9.2 Yes—get access token—if trusted authorization token request is made.

Access Token—depending on the subscriber and the content's metadata attributes, an authorization token is created.

10. Send—an access token is sent to the interface where the data is made (i.e., Interface 1).
11. Access Token—Interface 2 receives the access token.
12. Use access token to access data—Interface 2 evaluates the conditions of the metadata, applies access token to content and properly decrypts the content and views the data requested from the publisher complying with the policy.

Table 2, below, is a strengths, weakness, opportunities, and threats (SWOT) analysis demonstrating the benefits of this new systems model over present-day systems without a standard data schema encapsulation methodology.

TABLE 2

| Strengths: | Weaknesses: |
|---|---|
| Simple design (small number of actors) | Difficult to design a data schema for all intended uses |
| Scalable | Management of subscribers |
| Agile to rule changes about the data being exchanged | Data storage requirements |
| More control over data beyond original exchange and data resiliency | New concept and resistance |

| Opportunities: | Threats: |
|---|---|
| Data analytics/intelligence | Attacker-Malware |
| Faster to market with new products | Trusted insider |
| Data becomes a new revenue stream for services | |

Since the threats remain the same between the current methods of today (systems designs and models), the remaining items may become the differentiators for the techniques of this disclosure. Table 3 below indicates solutions to remediate potential weaknesses presented in the publisher-subscriber model and standard device data schema.

TABLE 3

| Weakness: | Remediation: |
|---|---|
| Difficult to design a data schema for all intended uses | With multiple types of publisher-subscriber models there common themes of data exchanges that have similar "tags" (e.g. file attributes have date created, accessed, modified, etc. as do photo files) may be developed. As more data exchanges are built, expertise and standards may be developed that help one design new schemas from others already in existence. In addition, if a poorly built data schema has to be modified or changed another publisher can be quickly built with the revisions and replace the current solution. |
| Management of subscribers-who has our data, for how long, do they still need it, what if the schema changes, etc. | Investment in lifecycle management of the subscribers to a data publishing service needs to be built and maintained. To support the success of this maintenance one may include a data attributes, during the exchange of data that may ensure service levels (contract schema) and subscribers' expectations and responsibilities. The point here is that the schema can be used to help eliminate this weakness. |
| Data storage requirements-Data encapsulation is the act of applying more attributes, key value pairs, and claims (e.g. policy) on data by cryptographic methods. This may inherently grow the size of data. | Leverage tiered storage model for the data that is stored at rest, this includes other technologies like de-duplication/single instance storage. It is important to note that as storage technologies improve the cost per gigabyte has consistently gone down to meet the needs of data growth. |
| New concept and resistance | A common challenge with change. Identify key stakeholder and thought leaders to isolate a sponsor to champion this effort. |

The publisher-subscriber model may be leveraged to prototype a sample use case representing a mock clinical trial. The purpose of the use case is to describe what data needs to be exchanged between the data repository safeguarding clinical trial data (the publisher) and the organization (the subscriber).

Figure 7:
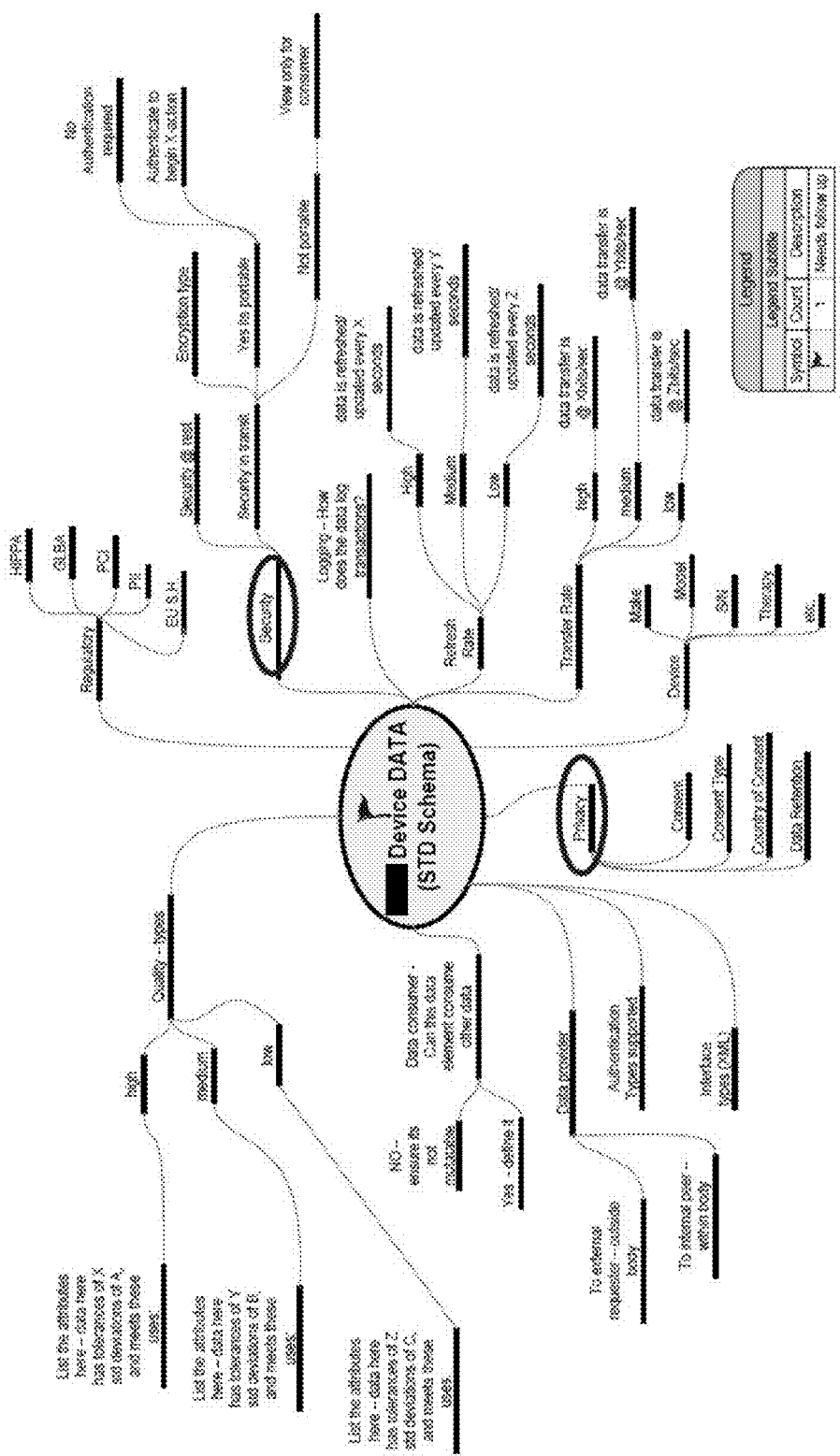
FIG. 7 is an example map to represent a sample of what types of metadata may be important as a subscriber, and as a publisher of data to be exchanged.

FIG. 7 is an example map to represent a sample of what types of metadata may be important as a subscriber, and as a publisher of data to be exchanged. A complete metadata schema may be created by both device data engineers, IT data and system engineers, and may be managed and maintained on a periodic basis to ensuring the schema is efficient, effective, and still performing as intended. The vision for a publishing warehouse of data may encourage a consortium of data engineers to actively measure the metadata schema for efficacy.

Again, one example goal is to place controls on the data to be exchanged, as close to the data source as possible. For the objectives of a pan-organization clinical project in accordance with one or more techniques of this disclosure, the focus is on privacy and security attributes, highlighted in the example of FIG. 7.

Inclusion of the security and privacy attributes may make data as resistant and resilient as possible for exchange in open, yet regulated, ecosystems. Below are the proposed lists of requirements (metadata key and value pairs) that map out the specific variables/attributes for the privacy and security domains to be added to the CDISC SDTM:

1. Improve the security, privacy, and value of device data during clinical trials.
   Identify technical safeguards for clinical data.
      E.g., confidentiality, integrity, AuthN/Z—See 3. security below for details
      Purpose—adds intrinsic value to data.
   Improve technical safeguards for clinical data.
      E.g., regulations required for the data=HIPAA/HITECH Safeguards
      Purpose—compliance and governance.
2. Add logic and context to data, as close to the authoring, to ensure proper intended use and sharing. That is at collection or other data exchanges:
   Ensure consent of data collected.
      E.g., yes or no.
      Purpose—did the subject provide consent for data policies?
   Identify the actual consent type obtained for the data collected.
      E.g., sell, publish, BI/BA.
   Know the country of consent.
      E.g., ISO3166—US=840.
      Purpose—additional rules for mapping to "what" publisher or subscriber is able to do with this the data exchanged.
   Know what date the consent is given and EOL for consent.
      E.g., begin=% date %, endofLife=% algorithm %.
      Purpose—data retention mapping to "how long", by end date, that publisher or subscriber can do "what" with the data exchanged.
3. Improve the security of the data collected.
   Classify the data.
      E.g., classification of the specific data exchanged.
      Purpose—Domain centric attributes tagging the exchange of data to and from publisher or subscriber.
   Implement the ability for authentication and authorization of data.
      E.g., identity and access control—from both a person and from a device perspective.
      Purpose—logging failed and successful access of data exchanged with respect to publisher and/or subscriber.
   Implement the ability for encryption of data at rest.
      E.g., yes or no.
      Purpose—does the data exchange require encryption for data at rest?
   Define the type of encryption at rest.
      E.g., ISO/IEC 18033 and 18033-3:2010.
      Purpose—specify the cipher and cipher strength.
   Implement the ability for encryption of data in transit or motion.
      E.g., yes or no.
      Purpose—does the data exchange require encryption for data in transit.
   Define the type of encryption for exchange.
      E.g., ISO/IEC 18033 and 18033-3:2010.
      Purpose—specify the cipher and cipher strength.

Figure 8:
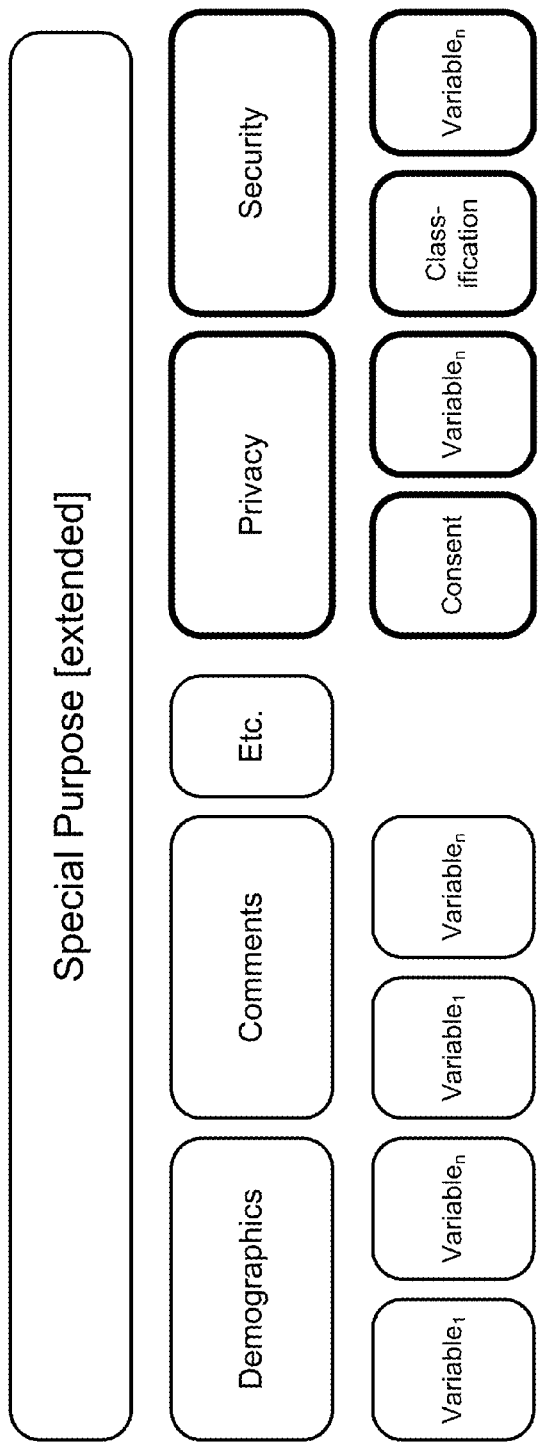
FIG. 8 is a conceptual diagram illustrating an example extension of the Clinical Data Standards Consortium's Study Data Tabulation Model.

Including these recommended schema attributes may transform the current SDTM (e.g., of FIG. 2) by expanding the "special purpose" category as shown in FIG. 8. In other words, FIG. 8 is a conceptual diagram illustrating an example extension of the CDISC SDTM. The data originator (the publisher of data) is responsible for generating the context, data schema determination, and attribute specifications. This schema information is shared, via industry standards (e.g. RESTFUL APIs or WSDL) and provides data with additional meaning and encapsulation when exchanged. More specifically, as the data is shared from publisher to subscriber, via their interfaces:

Metadata is read and/or acted upon.
Additional metadata may or may not be applied.
Rules or policies regarding metadata, and the data it is describing, can be logged, enforced, and events driven by these exchanges.

Finally, as IT systems change and become more integrated into the healthcare ecosystem, laws and policies may continue to evolve. Leveraging a standard set of device data schema, as proposed for clinical studies, may position an organization to react, recover, and focus on exchanging its data more securely and compliant with privacy concerns. This improved exchange of information may increase the capability, speed, and control of data transformations, analysis, and feedback into other IT systems to support the organization's mission and improve patients' outcomes.

Some findings are reviewed:

IT is becoming more pervasive (e.g. consumerization) and increasingly dependent upon reduced costs, improved efficiencies, and efficacy of healthcare ecosystems. Information systems built today to host, exchange, and control data (including device data) are progressively complex, inflexible to constant change, and vulnerable to increased risk.

Device data is a valuable asset. This asset becomes increasingly valuable as it is shared inside IT systems and with external IT systems that make up the healthcare environments.

A data driven systems model, using publisher-subscriber data exchanges built on a standard device data schema incorporating security and privacy attributes best positions the organization to support its mission and improve patient outcomes.

Below are the recommended short term (Table 4) and long term (Table 5) moves for the organization:

TABLE 4

| Short Term Moves | Why | Who | How | Cost/Benefit |
| --- | --- | --- | --- | --- |
| 1. Define a device data standard model- FIG. 7 is a start that may be iterated upon | Exposes common attributes across Devices-e.g. Security and Privacy | Systems Engineers, IT Data SMEs, and External Payer | Internal collaboration and brainstorming sessions. Begin with functional business processes that may benefit | Cost-6 FTEs for 1 month = XXX USD Benefit- point to begin and |

TABLE 4-continued

| Short Term Moves | Why | Who | How | Cost/Benefit |
|---|---|---|---|---|
| | | | from this standardization of data. e.g., supply chain, FDA submissions, BI/BA, etc. | start to define measures/ metrics to qualify assumptions |
| 2. Implement recommended pan-organization Privacy and Security Data Standard Schema for FDA Submissions- FIG. 8. | Make data more resilient, protected beyond intended use, and auditable | Clinical Business, Regulatory and compliance, IT SME | Execute the defined schema in organization's IT system warehousing clinical data (Publisher) and test the consumption of data (subscriber) via the new interfaces. Measure the submission to FDA and detail the true saving to the organization. | Cost-6 FTE for 1 month, 3 labs for 1 month, and XXX USD for interface development = YYY USD |
| 3. Refine and iterate this document from the results of short term moves 1&2. | Trend changes, uncertainties become clearer, and new measures & metrics may be identified. | Systems Engineer, Business Analyst, IT SME | Knowledge gained from the testing and implementation of the privacy and security standards may be evaluated for efficacy and periodically re-checked. | Cost-3 FTEs for 1 months = XXX USD Benefits- metrics and processes to monitor the standards of its lifecycle |

TABLE 5

Figure 9A:
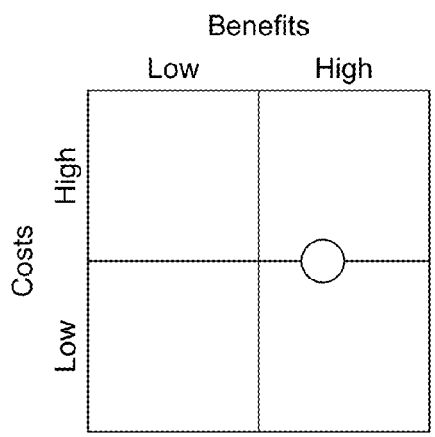
FIG. 9A is a conceptual diagram illustrating an example cost/benefit analysis, in accordance with one or more techniques of this disclosure.
Figure 9B:
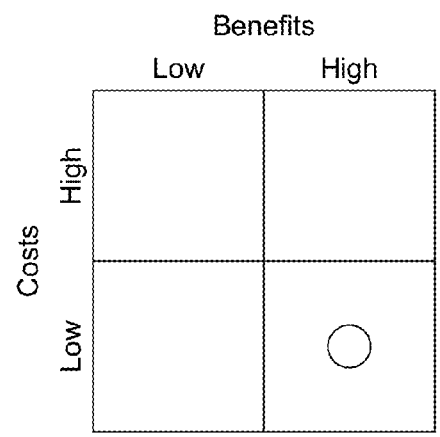
FIG. 9B is a conceptual diagram illustrating an example cost/benefit analysis, in accordance with one or more techniques of this disclosure.
Figure 9C:
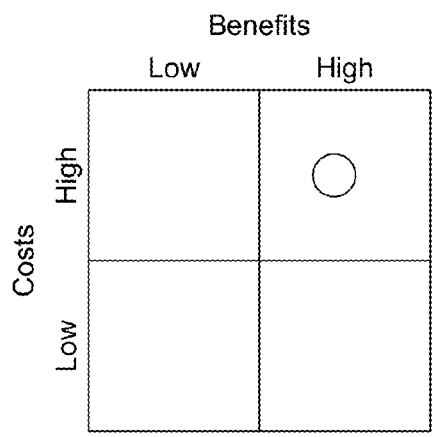
FIG. 9C is a conceptual diagram illustrating an example cost/benefit analysis, in accordance with one or more techniques of this disclosure.
Figure 9D:
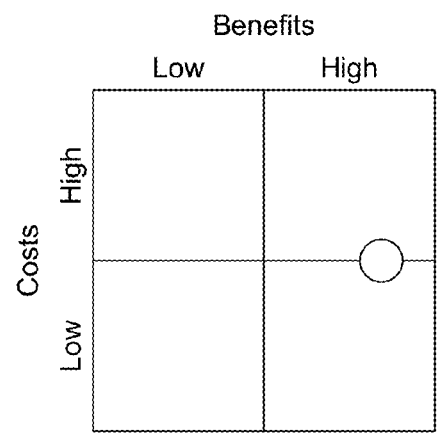
FIG. 9D is a conceptual diagram illustrating an example cost/benefit analysis, in accordance with one or more techniques of this disclosure.

| Long Term Moves | Why | Who | How | Cost/ Benefit |
|---|---|---|---|---|
| 1. Use the results obtained in short term moves to grow testing to external data domains (e.g. healthcare systems) and implantable medical devices in body. | Be a leader in this transformation, creating a competitive advantage with current devices, and improve speed to market for new devices, and therapies. | Systems Engineers, IT specialists, and key Partners | Leverage internal resources to expand our data warehouse to enable more data subscribers' access to this publishing source. Refine measures and metrics and audit usage. Duplicate process with external partner and refine strategy from results. | See FIG. 9A |
| 2. Begin "Red Teaming" the proposed design and data driven methodologies on a periodic basis. | Minimize gaps, new threats, and changing stakeholders. | Security Specialists, System Engineers, Legal, and Regulatory | Create a cross discipline team of subject matter experts. Duties of this team rotate quarterly to keep fresh ideas, and avoid stagnation, and attempt to exploit vulnerabilities within the design, technologies, and any new policies/laws that have changed since implementation. | See FIG. 9B |
| 3. Manage and maintain a roadmap of technologies and interfaces for the device data standard schema- reference architecture. | This ensures the success of the standard schema by applying feedback into the design as technologies, processes, and people change | Data Manager, External partners other device | Publish and share the standard device schema with manufactures to leverage, refine, and extend. Investigate the creation of an ISO standard/or Open specification. | See FIG. 9C |
| 4. Build a 3 year plan to grow scope of this model to other systems that interoperate with the device data | This ensures the data exchanges downstream from the originating device data are encapsulating its information. | Global IT, System Engineers, Legal, and Regulatory | Create a data consortium to develop a charter, mission, and roadmaps for data schema standards (domain specific) and receives feedback from the efforts of step #3. Result of roadmap may identify the greatest domain areas that may leverage the proposed standard data | See FIG. 9D |

TABLE 5-continued

| Long Term Moves | Why | Who | How | Cost/ Benefit |
|---|---|---|---|---|
| | | | schema and publisher-subscriber model-e.g. in body communications. | |

The techniques of this disclosure can be extended into other digital data domains: financial, military, energy, etc. As more domains are mapped, new task items may be defined to generalize these results into a periodic table of data domain standards with unique metadata for each domain, which enables higher order data exchanges in future cloud universes.

What are the risks to data? Definition of Risks=threats×vulnerabilities×consequences×probabilities Threats to the security of data are:
Trusted benevolent insiders—Employees, partners, contractors, and trusted persons.
Trusted malevolent insiders—Disgruntled employee, partner, contractor, or persons.
Attacker—Untrusted third party entity (e.g. hacker, nation state, organized crime, etc.) leveraging any insider or simply self-directed to obtain unauthorized access to your data.

NOTE: These are all people. Solutions are either training, education, or removal (e.g. via technology).

Vulnerabilities to the data are:
Business Processes—procedures that are dated and/or expose once secure data.
Data is not resilient on its own—if damaged or corrupted it cannot be trusted.
Data is not aware of context—e.g., data does not know that it is important or valuable, it only exists. For instance, system administrators can access data to perform a maintenance tasks and not know the meaning of the data. However, a non-administrator accessing the same data (understanding what the data represents) can now either perform a task, make a decision, or any other action for good or bad intent.
Data is not protected—placed in locations that are easily accessible and open.

NOTE: Data is like a child—by age 18 those parents that nurture, protect, and care for (in the case of data this may include frameworks, processes, and support systems) trust that they have educated and made resilient, capable, and accountable a functioning adult to help move society forward by replicating/improving from their experiences.

Figure 10:
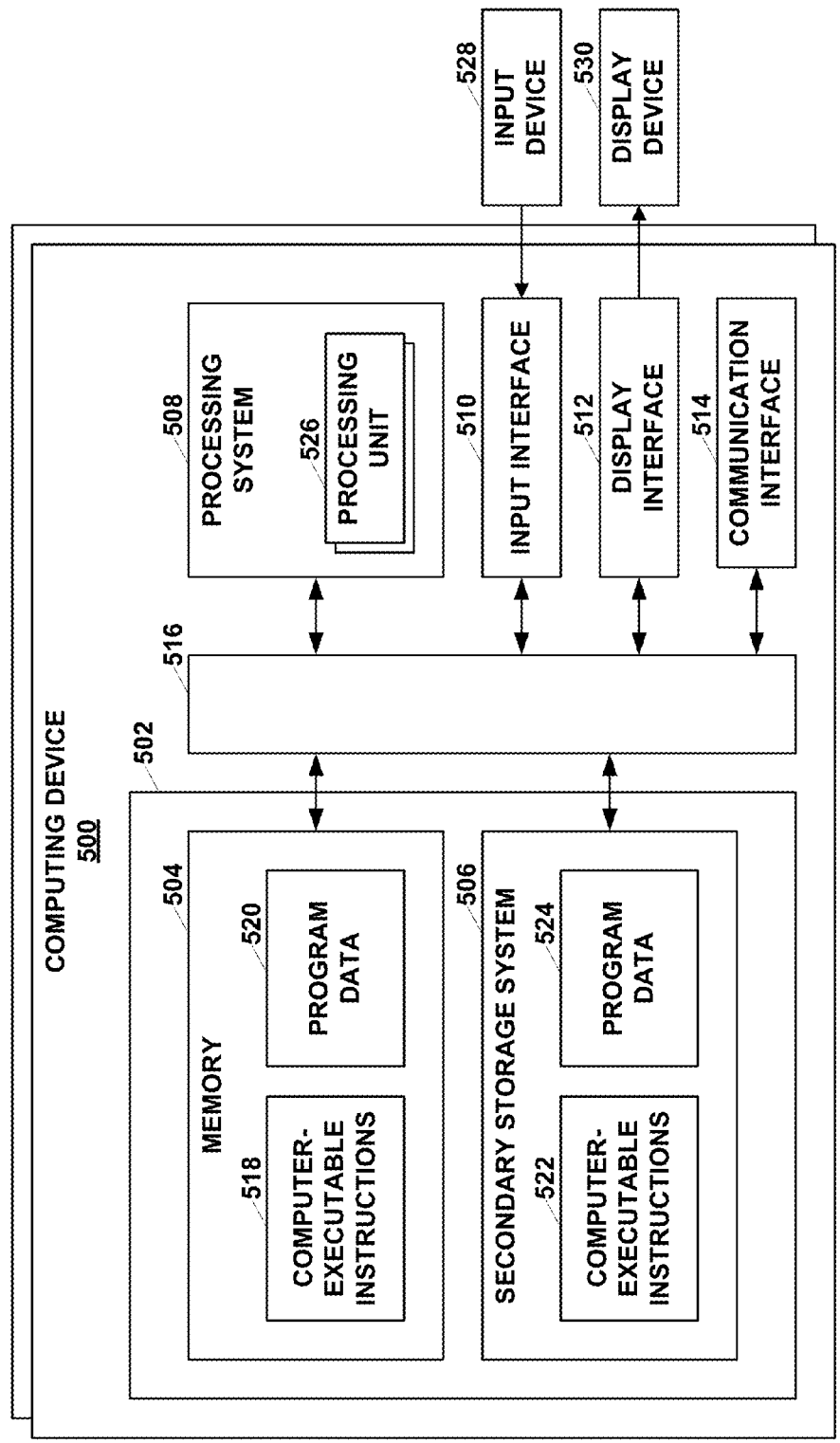
FIG. 10 is a conceptual block diagram that illustrates an example configuration of a computer system.

FIG. 10 is a block diagram of an example configuration of a computer system, in accordance with one or more techniques of this disclosure. In the example of FIG. 10, the computer system comprises a computing device 500 and one or more other computing devices. Computing device 500 may be a computing device in a data exchange system according to the techniques of this disclosure. For instance, computing device 500 of FIG. 10 may implement the publisher, the subscriber, Interface 1, or Interface 2 of FIG. 6. Furthermore, computing device 500 of FIG. 10 may implement one or more of the devices of human data domain 10, programmer data domain 12, personal device data domain 14, and cloud data domain 16 of FIG. 1.

Computing device 500 is a physical device that processes information. In the example of FIG. 10, computing device 500 comprises a data storage system 502, a memory 504, a secondary storage system 506, a processing system 508, an input interface 510, a display interface 512, a communication interface 514, and one or more communication media 516. Communication media 516 enable data communication between processing system 508, input interface 510, display interface 512, communication interface 514, memory 504, and secondary storage system 506. Computing device 500 can include components in addition to those shown in the example of FIG. 10. Furthermore, some computing devices do not include all of the components shown in the example of FIG. 10.

A computer-readable medium may be a medium from which a processing system can read data. Computer-readable media may include computer storage media and communications media. Computer storage media may include physical devices that store data for subsequent retrieval. Computer storage media are not transitory. For instance, computer storage media do not exclusively comprise propagated signals. Computer storage media may include volatile storage media and non-volatile storage media. Example types of computer storage media may include random-access memory (RAM) units, read-only memory (ROM) devices, solid state memory devices, optical discs (e.g., compact discs, DVDs, BluRay discs, etc.), magnetic disk drives, electrically-erasable programmable read-only memory (EEPROM), programmable read-only memory (PROM), magnetic tape drives, magnetic disks, and other types of devices that store data for subsequent retrieval. Communication media may include media over which one device can communicate data to another device. Example types of communication media may include communication networks, communications cables, wireless communication links, communication buses, and other media over which one device is able to communicate data to another device.

Data storage system 502 may be a system that stores data for subsequent retrieval. In the example of FIG. 10, data storage system 502 comprises memory 504 and secondary storage system 506. Memory 504 and secondary storage system 506 may store data for later retrieval. In the example of FIG. 10, memory 504 stores computer-executable instructions 518 and program data 520. Secondary storage system 506 stores computer-executable instructions 522 and program data 524. Physically, memory 504 and secondary storage system 506 may each comprise one or more computer storage media.

Processing system 508 is coupled to data storage system 502. Processing system 508 may read computer-executable instructions from data storage system 502 and executes the computer-executable instructions. Execution of the computer-executable instructions by processing system 508 may configure and/or cause computing device 500 to perform the actions indicated by the computer-executable instructions. For example, execution of the computer-executable instructions by processing system 508 can configure and/or cause computing device 500 to provide Basic Input/Output Systems, operating systems, system programs, application programs, or can configure and/or cause computing device 500 to provide other functionality.

Processing system 508 may read the computer-executable instructions from one or more computer-readable media. For example, processing system 508 may read and execute computer-executable instructions 518 and 522 stored on memory 504 and secondary storage system 506.

Processing system 508 may comprise one or more processing units 526. Processing units 526 may comprise physical devices that execute computer-executable instructions.

Processing units 526 may comprise various types of physical devices that execute computer-executable instructions. For example, one or more of processing units 526 may comprise a microprocessor, a processing core within a microprocessor, a digital signal processor, a graphics processing unit, or another type of physical device that executes computer-executable instructions.

Input interface 510 may enable computing device 500 to receive input from an input device 528. Input device 528 may comprise a device that receives input from a user. Input device 528 may comprise various types of devices that receive input from users. For example, input device 528 may comprise a keyboard, a touch screen, a mouse, a microphone, a keypad, a joystick, a brain-computer interface device, or another type of device that receives input from a user. In some examples, input device 528 is integrated into a housing of computing device 500. In other examples, input device 528 is outside a housing of computing device 500.

Display interface 512 may enable computing device 500 to display output on a display device 530. Display device 530 may be a device that displays output. Example types of display devices include monitors, touch screens, display screens, televisions, and other types of devices that display output. In some examples, display device 530 is integrated into a housing of computing device 500. In other examples, display device 530 is outside a housing of computing device 500.

Communication interface 514 may enable computing device 500 to send and receive data over one or more communication media. Communication interface 514 may comprise various types of devices. For example, communication interface 514 may comprise a Network Interface Card (NIC), a wireless network adapter, a Universal Serial Bus (USB) port, or another type of device that enables computing device 500 to send and receive data over one or more communication media.

In accordance with some examples of this disclosure, communication interface 514 may receive or send a metadata envelope that conforms to a schema that defines each allowable metadata attribute of the metadata envelope. Responsive to communication interface 514 receiving the metadata envelope, processing system 508 may determine, based at least in part on a first metadata attribute of the received metadata envelope, a particular patient data handling policy from among a plurality of available patient data handling policies that the interface is configured to apply. Each of the available patient data handling policies prescribes a different way of handling patient data. Furthermore, processing system 508 may apply the particular patient data handling policy with regard to a particular set of patient data encapsulated within the received metadata envelope. When the particular patient data handling policy indicates that authorization is required in order to access the particular set of patient data, processing system 508 may request, via communication interface 514, from an authorization service identified by a second metadata attribute of the received metadata envelope, authorization to access the particular set of patient data. In some examples, processing system 508 may perform these actions when processing system 508 executes computer-executable instructions 518 and/or 522, which are stored on computer-readable data storage media.

Figure 11:
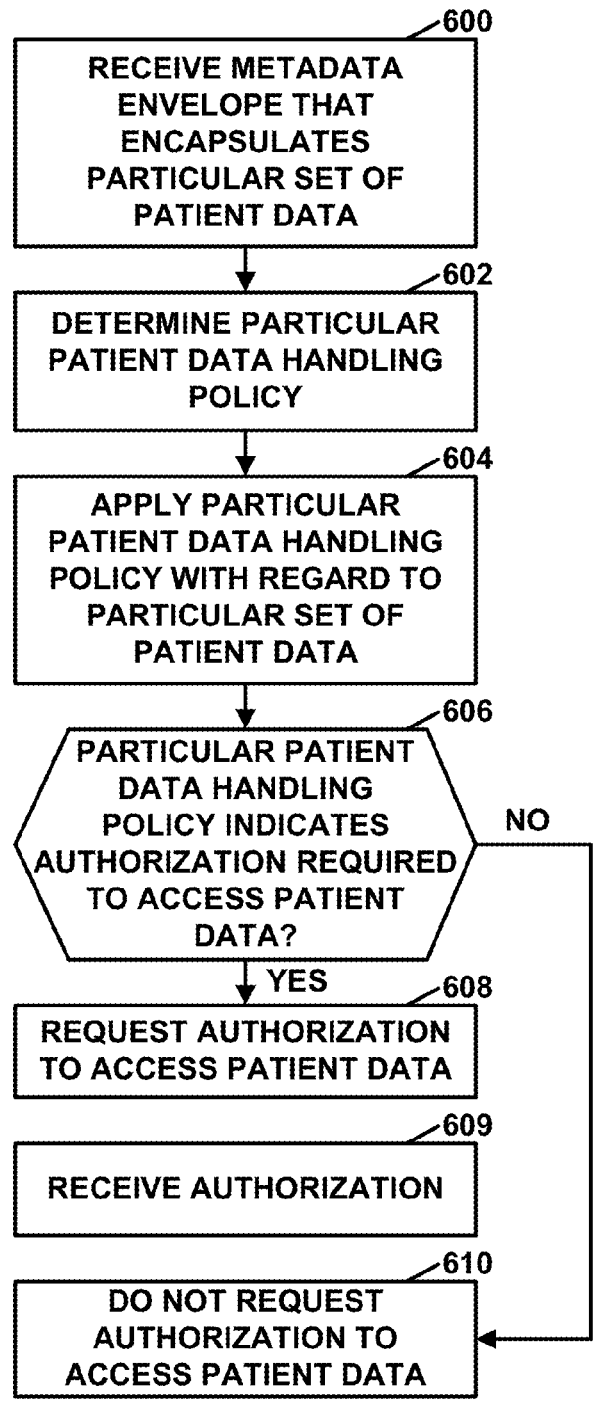
FIG. 11 is a flowchart illustrating an example operation of a subscriber interface, in accordance with one or more example techniques of this disclosure.

FIG. 11 is a flowchart illustrating an example operation of a subscriber interface, in accordance with one or more example techniques of this disclosure. In the example of FIG. 11, a subscriber interface implemented by a device may receive a metadata envelope that encapsulates a particular set of patient data associated with a patient (600). The metadata envelope may conform to a schema that defines each allowable metadata attribute of the metadata envelope. Furthermore, the subscriber interface may determine, based at least in part on a first metadata attribute of the received metadata envelope, a particular patient data handling policy from among a plurality of available patient data handling policies that the interface is configured to apply (602). In some examples, the plurality of available patient data handling policies is preconfigured at the subscriber interface. In some such examples, each respective available patient data handling policy has a corresponding index. In some such examples, the first metadata attribute may specify an index corresponding to the particular patient data handling policy. Each of the available patient data handling policies may prescribe a different way of handling patient data. For example, one or more of the patient data handling policies may require the deletion of the patient data after a particular amount of time has passed. In another example, one or more of the patient data handling policies may indicate that only people with particular credentials may access the patient data. In another example, one or more of the patient data handling policies may indicate that the subscriber interface should not have the patient data and that the patient data should therefore be deleted. In addition, the subscriber interface may apply the particular patient data handling policy with regard to the particular set of patient data (604).

Furthermore, the subscriber interface may determine whether the particular patient data handling policy indicates that authorization is required in order to access the particular set of patient data (606). When the particular patient data handling policy indicates that receiving authorization is required in order to access the particular set of patient data ("YES" of 606), the subscriber interface may request, from an authorization service identified by a second metadata attribute of the received metadata envelope, authorization to access the particular set of patient data (608). Subsequently, the subscriber interface may or may not receive the authorization to access the particular set of patient data (609). In some examples, such as the example of FIG. 11, when the particular patient data handling policy indicates that authorization is not required in order to access the particular set of patient data ("NO" of 606), the subscriber interface does not request authorization to access the particular set of patient data (610). Furthermore, in some examples where the particular patient data handling policy indicates that authorization is required in order to access the particular set of patient data, the subscriber interface may perform some other action, such as directly accessing the particular set of patient data.

The following paragraphs describe various examples of the techniques of this disclosure.

Example 1. A system for exchanging patient data, the system comprising: at least one device that implements an interface, wherein when the interface receives a metadata envelope that conforms to a schema that defines each allowable metadata attribute of the metadata envelope: the interface determines, based at least in part on a first metadata attribute of the received metadata envelope, a particular patient data handling policy from among a plurality of available patient data handling policies that the interface is configured to apply, wherein each of the available patient data handling policies prescribes a different way of handling patient data; and the interface applies the particular patient data handling policy with regard to a particular set of patient data encapsulated within the received metadata envelope, wherein when the particular patient data handling policy indicates that receiving authorization is required in order to access the particular set of patient data, the interface requests, to receive from an authorization service identified by a second metadata attribute of the received metadata envelope, the authorization to access the particular set of patient data.

Example 2. The system of example 1, wherein the at least one device includes at least one implantable medical device.

Example 3. The system of examples 1 or 2, wherein the at least one device includes at least one programmer device for an implantable medical device.

Example 4. The system of any of examples 1-3, wherein the interface receives the authorization to access the particular set of patient data only when the interface provides evidence to the authorization service that the interface is configured such that the interface does not transmit the particular set of patient data in encrypted or unencrypted form outside the metadata envelope and does not generate copies of the particular set of patient data in unencrypted form that persist after termination of the interface.

Example 5. The system of example 4, wherein: the evidence comprises authorization data encrypted according to an encryption key, and a requirement to receive a decryption key for the particular set of patient data to the interface from the authorization service is that the authorization service is able to successfully decrypt the authorization data.

Example 6. The system of any of examples 1-5, wherein the particular set of patient data comprises clinical study data.

Example 7. The system of any of examples 1-6, wherein the first metadata attribute indicates a governmental regulation applicable to the particular set of patient data.

Example 8. The system of any of examples 1-7, wherein the first metadata attribute or an additional metadata attribute of the metadata envelope indicates a type of consent given by a patient regarding sharing of the particular set of patient data.

Example 9. The system of any of examples 1-8, wherein the first metadata attribute or an additional metadata attribute of the metadata envelope indicates a country in which consent was given by a patient regarding sharing of the particular set of patient data.

Example 10. The system of any of examples 1-9, wherein the interface is further configured to: determine, based on the particular patient data handling policy, whether to delete the particular set of patient data; and delete, based on the determination, the particular set of patient data.

Example 11. The system of any of examples 1-10, wherein the metadata envelope includes a third metadata attribute, the third metadata attribute indicating a type of encryption applied to the particular set of patient data.

Example 12. The system of any of examples 1-11, wherein the metadata envelope includes a third metadata attribute, the third metadata attribute indicating a source of the particular set of patient data.

Example 13. The system of any of examples 1-12, wherein: the particular set of patient data is a first set of patient data and the metadata envelope is a first metadata envelope, and when the interface publishes a second set of patient data, the interface encapsulates the second set of patient data within a second metadata envelope that includes one or more metadata attributes, wherein the second metadata envelope conforms to the schema.

Example 14. The system of any of examples 1-13, wherein the schema is an extension of a Study Data Tabulation Model.

Example 15. A method of handling (e.g., exchanging) patient data, the method comprising: receiving, at an interface implemented by a device, a metadata envelope that encapsulates a particular set of patient data associated with a patient, wherein the metadata envelope conforms to a schema that defines each allowable metadata attribute of the metadata envelope; determining, by the interface, based at least in part on a first metadata attribute of the received metadata envelope, a particular patient data handling policy from among a plurality of available patient data handling policies that the interface is configured to apply, wherein each of the available patient data handling policies prescribes a different way of handling patient data; and applying, by the interface, the particular patient data handling policy with regard to the particular set of patient data, wherein when the particular patient data handling policy indicates receiving authorization is required in order to access the particular set of patient data, requesting, by the interface, from an authorization service identified by a second metadata attribute of the received metadata envelope, to receive the authorization to access the particular set of patient data.

Example 16. The method of example 15, wherein the device is an implantable medical device.

Example 17. The method of examples 15 or 16, wherein the device is a programmer device for an implantable medical device.

Example 18. The method of any of examples 15-17, wherein the interface receives the authorization to access the particular set of patient data only when the interface provides evidence to the authorization service that the interface is configured such that the interface does not transmit the particular set of patient data in encrypted or unencrypted form outside the metadata envelope and does not generate copies of the particular set of patient data in unencrypted form that persist after termination of the interface.

Example 19. The method of example 18, wherein: the evidence comprises authorization data encrypted according to an encryption key, and a requirement for receiving a decryption key for the particular set of patient data to the interface from the authorization service is that the authorization service is able to successfully decrypt the authorization data.

Example 20. The method of any of examples 15-19, wherein the particular set of patient data comprises clinical study data.

Example 21. The method of any of examples 15-20, wherein the first metadata attribute indicates a governmental regulation applicable to the particular set of patient data.

Example 22. The method of any of examples 15-21, wherein the first metadata attribute or an additional metadata attribute of the metadata envelope indicates a type of consent given by a patient regarding sharing of the particular set of patient data.

Example 23. The method of any of examples 15-22, wherein the first metadata attribute or an additional metadata attribute of the metadata envelope indicates a country in which consent was given by the patient regarding sharing of the particular set of patient data.

Example 24. The method of any of examples 15-23, wherein the interface is further configured to: determine, based on the particular patient data handling policy, whether to delete the particular set of patient data; and delete, based on the determination, the particular set of patient data.

Example 25. The method of any of examples 15-24, wherein the metadata envelope includes a third metadata attribute, the third metadata attribute indicating a type of encryption applied to the particular set of patient data.

Example 26. The method of any of examples 15-25, wherein the metadata envelope includes a third metadata attribute, the third metadata attribute indicating a source of the particular set of patient data.

Example 27. The method of any of examples 15-26, wherein the schema is an extension of a Study Data Tabulation Model.

Example 28. A computer-readable data storage medium having instructions stored thereon that, when executed, configure an interface implemented by a device to: receive a metadata envelope that encapsulates a particular set of patient data associated with a patient, wherein the metadata envelope conforms to a schema that defines each allowable metadata attribute of the metadata envelope; determine based at least in part on a first metadata attribute of the received metadata envelope, a particular patient data handling policy from among a plurality of available patient data handling policies that the interface is configured to apply, wherein each of the available patient data handling policies prescribes a different way of handling patient data; and apply the particular patient data handling policy with regard to the particular set of patient data, wherein when the particular patient data handling policy indicates receiving authorization is required in order to access the particular set of patient data, request, to receive from an authorization service identified by a second metadata attribute of the received metadata envelope, the authorization to access the particular set of patient data.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer-readable medium, such as a computer-readable storage medium, containing instructions. Instructions embedded or encoded in a computer-readable medium, including a computer-readable storage medium, may cause one or more programmable processors, or other processors, to implement one or more of the techniques described herein, such as when instructions included or encoded in the computer-readable medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may comprise one or more computer-readable storage media.

Various examples have been described. These and other examples are within the scope of the following claims.

What is claimed is:

1. A data warehouse system, the system comprising:
at least one processing circuitry configured to:
encapsulate, within a respective metadata envelope, each data record from a set of data records for a clinical study by:
adding, to the metadata envelope, at least one class component that defines the clinical study;
adding, to the metadata envelope, at least one domain component that defines details of a subject within the clinical study;
adding, to the metadata envelope, at least one variable component that defines data gathered during the clinical study;
adding, to the metadata envelope, at least one privacy component that defines usage safeguards on access to the data record; and
adding, to the metadata envelope, at least one security component that defines protection from security threats;
receive a request for a particular data record from the set of clinical study data records from a subscriber interface;
determine whether the subscriber interface satisfies the protection from security threats as defined in the security component of the particular data record;
transmit, in response to determining that the subscriber interface satisfies the protection from security threats; the encapsulated particular data record to the subscriber interface;
receive a request for an authorization token from the subscriber interface and for the encapsulated particular data record;
verify trust of the subscriber interface;
in response to verifying trust, create the authorization token, the authorization token providing an access right to the encapsulated particular data, wherein the authorization token is created dependent upon attributes of the metadata components and the subscriber interface, and
transmit the authorization token to the subscriber interface to apply to the encapsulated particular data for access thereto.

2. The system of claim 1, wherein the system is further configured to provide a security authorization service and wherein the at least one privacy component includes an identification of the security authorization service.

3. The system of claim 2, wherein the security authorization service is configured to receive encrypted authorization data from the subscriber interface.

4. The system of claim 3, wherein the security authorization service is further configured to determine whether the subscriber interface satisfies the protection from security threats as defined in the security component of the particular data record by decrypting the encrypted authorization data.

5. The system of claim 1, wherein the at least one privacy component indicates a type of consent given by a patient regarding sharing of the particular set of patient data.

6. The system of claim 1, wherein the at least one privacy component indicates a country in which consent was given by a patient regarding sharing of the particular set of patient data.

7. The system of claim 1, wherein the at least one processing circuitry is further configured to share schema information about the metadata envelopes.

8. The system of claim 1, wherein the at least one processing circuitry is further configured to modify the schema information about the metadata envelopes in response to a change to requirements to privacy or security.

9. The system of claim 1, wherein the at least one security component specifies whether the set of data records are to be encrypted by the subscriber interface when the data is at rest.

10. The system of claim 9, wherein the at least one security component specifies the type of encryption to be used by the subscriber interface when the data is at rest.

11. A method for use with a data warehouse system having at least one processing circuitry, the method comprising:
    using the at least one processing circuitry to:
        encapsulate, within a respective metadata envelope, each data record from a set of data records for a clinical study by:
            adding, to the metadata envelope, at least one class component that defines the clinical study;
            adding, to the metadata envelope, at least one domain component that defines details of a subject within the clinical study;
            adding, to the metadata envelope, at least one variable component that defines data gathered during the clinical study;
            adding, to the metadata envelope, at least one privacy component that defines usage safeguards on access to the data record; and
            adding, to the metadata envelope, at least one security component that defines protection from security threats;
        receive a request for a particular data record from the set of clinical study data records from a subscriber interface;
        determine whether the subscriber interface satisfies the protection from security threats as defined in the security component of the particular data record;
        transmit, in response to determining that the subscriber interface satisfies the protection from security threats; the encapsulated particular data record to the subscriber interface;
        receive a request for an authorization token from the subscriber interface and for the encapsulated particular data record;
        verify trust of the subscriber interface;
        in response to verifying trust, create the authorization token, the authorization token providing an access right to the encapsulated particular data, wherein the authorization token is created dependent upon attributes of the metadata components and the subscriber interface, and
        transmit the authorization token to the subscriber interface to apply to the encapsulated particular data for access thereto.

12. The method of claim 11, wherein the at least one privacy component includes an identification of a security authorization service.

13. The method of claim 12, further comprising receiving, by the security authorization service, encrypted authorization data from the subscriber interface.

14. The method of claim 13, further comprising determining, by the security authorization service, whether the subscriber interface satisfies the protection from security threats as defined in the security component of the particular data record by decrypting the encrypted authorization data.

15. The method of claim 11, wherein the at least one privacy component indicates a type of consent given by a patient regarding sharing of the particular set of patient data.

16. The method of claim 11, wherein the at least one privacy component indicates a country in which consent was given by a patient regarding sharing of the particular set of patient data.

17. The method of claim 11, further comprising sharing, using the at least one processing circuitry and with subscriber interfaces, schema information about the metadata envelopes.

18. The method of claim 11, further comprising modifying, using the at least one processing circuitry, the schema information about the metadata envelopes in response to a change to requirements to privacy or security.

19. The method of claim 11, wherein the at least one security component specifies whether the set of data records are to be encrypted by the subscriber interface when the data is at rest.

20. The method of claim 19, wherein the at least one security component specifies the type of encryption to be used by the subscriber interface when the data is at rest.

* * * * *